(12) United States Patent
Kuki et al.

(10) Patent No.: US 7,138,408 B2
(45) Date of Patent: Nov. 21, 2006

(54) HIV INTEGRASE INHIBITORS, PHARMACEUTICAL COMPOSITIONS AND METHODS FOR THEIR USE

(75) Inventors: Atsuo Kuki, Encinitas, CA (US); Xinqiang Li, San Diego, CA (US); Michael Bruno Plewe, San Diego, CA (US); Hai Wang, San Diego, CA (US); Junhu Zhang, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/251,344

(22) Filed: Oct. 14, 2005

(65) Prior Publication Data

US 2006/0122211 A1    Jun. 8, 2006

Related U.S. Application Data

(62) Division of application No. 10/765,227, filed on Jan. 26, 2004, now Pat. No. 7,001,912.

(60) Provisional application No. 60/443,223, filed on Jan. 27, 2003.

(51) Int. Cl.
*A61K 31/437* (2006.01)
*C07D 471/12* (2006.01)

(52) U.S. Cl. ..................... 514/287; 546/64; 540/521; 514/215

(58) Field of Classification Search ............... 514/287, 514/215; 546/64; 540/521
See application file for complete search history.

(56) References Cited

U.S. PATENT DOCUMENTS

| 4,371,536 A | 2/1983 | Braestrup et al. |
| 5,010,077 A | 4/1991 | Braestrup et al. |
| 6,057,297 A | 5/2000 | Politi et al. |
| 6,075,021 A | 6/2000 | Evanno et al. |

FOREIGN PATENT DOCUMENTS

| EP | 0 030 254 A | 8/1980 |
| EP | 1 209 158 A | 11/2000 |
| EP | 1 086 101 B1 | 3/2001 |
| EP | 1 375 486 A | 1/2004 |
| GB | 2 209 032 A | 4/1989 |
| JP | 2003119137 | 4/2003 |
| JP | 2003171381 | 6/2003 |
| WO | WO 99/64420 | 12/1999 |
| WO | WO 02/070491 | 9/2002 |
| WO | WO 03/033496 A | 4/2003 |
| WO | WO 03/035076 | 5/2003 |
| WO | WO 03/035076 A | 5/2003 |
| WO | WO 03/047564 | 6/2003 |
| WO | WO 03/049690 | 6/2003 |
| WO | WO 03/062204 | 7/2003 |
| WO | WO 03/077850 A | 9/2003 |
| WO | WO 2004/039803 A | 5/2004 |
| WO | WO 2004/067531 A | 8/2004 |

OTHER PUBLICATIONS

Ho, B., et al., "Inhibitors of Monoamine Oxidase: Influence of Methyl Substitution on the Inhibiting Activity of Beta-Carbolines," *J. Pharm. Sci.*, vol. 57, p. 269-274 (Feb. 1968), at p. 270, Table II (cmpd XX, XXII); and col. 1, line 21 et seq.

Ho, B., et al., "Inhibitors of Monoamine Oxidase III: 9-Substituted beta-Carbolines," *J. Pharm. Sci.*, vol. 58(2), pp. 219-221 (Feb. 1969), at p. 219, col. 1, lines 1-8, et seq.

Batch, A., and Dodd, R., "Ortho-Directed Metalation of 3-Carboxy-beta-carbolines," *J. Org. Chem.*, vol. 63, pp. 872-877 (1998), especially p. 872, cmpds 2 and 5.

Schlecker, W., et al., "Synthesis of 4-arylpyridines and Substituted beta-carbolines," *Tetrahedron*, vol. 51(35), pp. 9531-9542 (1995), especially p. 9535, cmpds 21, 22.

Mehta, A., and Dodd, R., "Ortho-Directed Lithiation Studies of 3-Carboxy-Beta-carbolines," *J.Org. Chem.*, vol. 58, pp. 7587-7590 (1993), especially at p. 7588, compounds 8,9,18, and 19.

U.S. Appl. No. 10/699,068, filed Oct. 30, 2003, Agouron Pharmaceuticals, Inc.

Abdel-Magid, et al., "Reductive Amination of Aldehydes And Ketones With Sodium Triacetoxyborohydride. Studies On Direct And Indirect Reductive Amination Procedures," *Journal of Organic Chemistry*, 1996, p. 3849-3862, vol. 61.

(Continued)

*Primary Examiner*—Charanjit S. Aulakh
(74) *Attorney, Agent, or Firm*—Jeffrey H. Tidwell; Bryan C. Zielinski

(57) ABSTRACT

Beta-carboline hydroxamic acid compounds represented by formula (I)

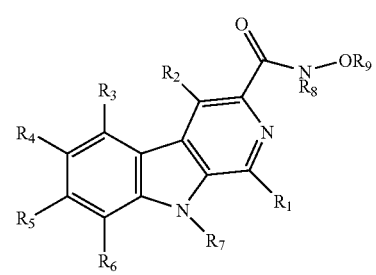

are described. The beta-carboline hydroxamic acid compounds and compositions containing those compounds may be used to inhibit or modulate the activity of HIV integrase enzyme and to treat HIV integrase-mediated diseases and conditions.

2 Claims, No Drawings

OTHER PUBLICATIONS

Bagshawe, K. et. al., "Antibody-Directed Enzyme Prodrug Therapy: A Review," *Drug. Development Research*, 1995, p. 220-230, vol. 34.

Barbier, C., et al., "Preparation of Lavendamycin Analogues," *Heterocycles*, 2000, p. 37-48, vol. 53, No. 1.

Bertolini, G. et. al., "A New Rational Hypothesis for the Pharmacophore of the Active Metabolite of Lefluonomide, a Potent Immunosuppressive Drug," *J. Med. Chem.*, 1997, p. 2011-2016, vol. 40.

Biere, H., et al., "Eine Neue und Besonders Einfache Synthese Von Zentralaktiven β-Carbolin-Derivaten," *Liebigs Ann. Chem.*, 1986, p. 1749-1764 (see English abstract).

Bodor, N, "Novel Approaches to the Design of Safer Drugs: Soft Drugs and Site-Specific Chemical Delivery Systems," *Advances in Drug Research*, 1984, p. 255-331, vol. 13.

Bundgaard, et al., *Design of Prodrugs*, 1985, Elsevier Press.

Bundgaard, H. "Design and Application of Prodrugs", *Drug Design Application and Development*, 1991.

Butler, S.L., et al., "A Quantitative Assay for HIV DNA Integration In Vivo," *Nature Medicine*, May 2001, p. 631-634, vol. 7, No. 5.

Campbell, K.N., et al., "The Preparation of Unsymmetrical Secondary Aliphatic Amines," *J. Am. Chem. Soc.*, 1944, p. 82-84, vol. 66.

Chen, B. et al., "Distinct Modes Of Human Immunodeficiency Virus Type 1 Proviral Latency Revealed By Superinfection Of Nonproductively Infected Cell Lines With Recombinant Luciferase-Encoding Viruses," *Journal of Virology*, 1994, p. 654-660, vol. 68, No. 2.

Dear, G.J. et. al., "Mass Directed Peak Selection, an Efficient Method of Drug Metabolite Identification Using Directly Coupled Liquid Chromatography-Mass Spectrometry-Nuclear Magnetic Resonance Spectroscopy," *Journal of Chromatography B*, 2000, p. 281-293, vol. 748.

Debyser, Z., et al., "*Assays for the Evaluation of HIV-1 Integrase Inhibitors,*" *Methods in Molecular Biology 160*, p. 139-155. Schein, C.H., Humana Press Inc., Totawa, NJ 2001.

Dekhane, M., et al., "A New Efficient Synthesis of Ethyl β-Carboline-3-Carboxylate (β-CCE) and Methyl 4-Methyl-β-Carboline-3-Carboxylate (4-Methyl-β-CCM) Starting From Indole-2 Carbolxaldehyde," *Tetrahedron*, 1994, p. 6299-6306, vol. 50, No. 21.

Doyle, et al., "Nuclear Analogs of β-lactam Antibiotics. I. Synthesis of O-2-isocephams," *Can. J. Chem.*, 1977, p. 468-483, vol. 55.

Eberle, M., "Contribution To The Chemistry Of Indole. About The 5-(1-Indolyl)-2-Pentanone System," *Journal of Organic Chemistry*, 1976, p. 633-636, vol. 41, No. 4.

Eliel, E.L., et al., *Stereochemistry of Organic Compounds*, Wiley, New York, 1994.

Erofeev, Y.V., et al., "Introduction of 3-Indolymethyl Residues in Nitroacetic Acid Esters," *Khim. Get. Soed.*, 1978, p. 780.

Goldgur, Y., et al., "Structure Of The HIV-1 Integrase Catalytic Domain Complexed With An Inhibitor: A Platform For Antiviral Drug Design," *PNAS*, Nov. 9, 1999, p. 13040-13043, vol. 96, No. 23.

Grobler, J. et al., "Diketo Acid Inhibitor Mechanism And HIV-1 Integrase: Implications For Metal Binding In The Active Site Of Phosphotransferase Enzymes," *PNAS*, May 14, 2002, p. 6661-6666, vol. 99, No. 10.

Hansen, M.S., et al., "Integration Complexes Derived From HIV Vectors For Rapid Assays In Vitro," *Nature Biotechnology*, Jun. 1999, p. 578-582, vol. 17, No. 6.

Hauser, C.R., et al., *Org. Synth. Coll.*, vol. 2, 1943, p. 67, John Wiley, New York.

Hazuda, D. et al., "Discovery And Analysis Of Inhibitors Of The Human Immunodeficiency Integrase," *Drug Design And Discovery*, 1997, p. 17-24, vol. 15.

Jenkins, T.M., et al., "A Soluble Active Mutant of HIV-1 Integrase," *Journal of Biological Chemistry*, 1996, p. 7712-7718, vol. 271, No. 13.

Kantlehner, W., et al., "Umsetzungen von *tert*-Butoxy-N,N,N',N'-tetramethylmethandiamin mit Nh- und CH-aciden Verbindungen," *Liebigs Ann. Chem.*, 1980, p. 344 (see English abstract).

Lewin, S.R., et al., "Use of Real-Time PCR and Molecular Beacons to Detect Virus Replication in Human Immunodeficiency Virus Type 1-Infected Individuals on Prolonged Effective Antiretroviral Therapy," *Journal of Virology*, Jul. 1999, p. 6099-6103, vol. 73, No. 7.

Lyttle, D.A., et al., "The Chemistry of Nitroacetic Acid and Its Esters. I. The Alkylation of Alkylnitroacetates with Gramine," *J. Am. Chem. Soc.*, 1947, p. 2118-2119, vol. 69.

March, Jerry, *Advanced Organic Chemistry*, 5th Edition, p. 508-511, John Wiley & Sons, 2001.

Neef, G., et al., "Synthesis of 4-Substituted β-Carbolines," *Heterocycles*, 1983, p. 1295-1313, vol. 20, No. 7.

Pais, G., et al., "Structure Activity of 3-Aryl-1,3-diketo-Containing Compounds as HIV-1 Integrase Inhibitors," Journal of Medicinal Chemistry, 2002, p. 3184-3194, vol. 45.

Prox, et. al., "Rapid Structure Elucidation of Drug Metabolites by Use of Stable Isotopes," *Xenobiotica*, 1973, p. 103-112, vol. 3, No. 2.

Sandrin, J., et al., "Pictet-Spengler Condensations in Refluxing Benzene," *Heterocycles*, 1976, p. 1101-1104, vol. 4, No. 6.

Sayasith, K., et al., "Targeting HIV-1 Integrase," *Expert Opin. Ther. Targets*, 2001, p. 443-464, vol. 5, No. 4.

Settimj, et al., "β-Carbolines as Agonistic or Antagonistic Benzodiazepine Receptor Ligands. 1. Synthesis of some 5-, 6- and 7-Amino Derivatives of 3-Methoxycarbonyl-β-carboline (β-CCM) and of 3-Ethoxycarbonyl-β-Carboline (β-CCE,)" *J. Heterocycl. Chem.*, 1988, p. 1391-1397, vol. 25.

Shan, D. et al., "Prodrug Strategies Based On Intramolecular Cyclization Reactions," *J. Pharm. Sci.*, 1997, p. 765-767, vol. 86, No. 7.

Snyder, H.R., et al., "The Synthesis of the 2-Amino-3-(3-indolyl)-butyric Acids (β-Methyltryptophans)," *J. Am. Chem. Soc.*, 1957, p. 2217-2221, vol. 79.

Spraul, et al., "Liquid Chromatography Coupled with High-Field Proton NMR for Profiling Human Urine for Endogenous Compounds and Drug Metabolites", *J. Pharmaceutical & Biomedical Analysis*, 1992, p. 601-605, vol. 10, No. 8.

Still, W., et al., "Rapid Chromatographic Technique For Preparative Separations With Moderate Resolution," *Journal of Organic Chemistry*, 1978, p. 2923-2925, vol. 43, No. 14.

Sundberg, et al., "Syntheses With N-Protected 2-Lithioindoles," *Journal of Organic Chemistry*, 1973, p. 3324-3330, vol. 38, No. 19.

Terwilliger, E.F., et al., "Construction and Use of a Replication-Competent Human Immunodeficiency Virus (HIV-1) That Expresses the Chloramphenicol acetyltransferase Enzyme," *Proc. Natl. Acad. Sci., USA*, May 1989, p. 3857-3861, vol. 86.

Wai, J. et al., "4-Aryl-2,4-Dioxobutanoic Acid Inhibitors Of HIV-1 Integrase And Viral Replication In Cells," *Journal of Medicinal Chemistry*, Dec. 28, 2000, p. 4923-4926, vol. 43, No. 26.

Weislow, O.S., et al., "New Soluble-Formazan Assay for HIV-1 Cytopathic Effects: Application to High-Flux Screening of Synthetic and Natural Products for AIDS-Antiviral Activity," *J. Natl. Cancer Inst.*, Apr. 19, 1989, p. 577-586, vol. 81, No. 8.

Young, S.D., et al., "Inhibition of HIV-1Integrase by Small Molecules: The Potential for a New Class of AIDS Chemotherapeutics," *Curr. Opin. Drug Disc. & Devel.*, 2001, p. 402-410, vol. 4, No. 4.

Young, S., et al., "L-870, 810: A Potent Antiviral HIV Integrase Inhibitor with Potential Clinical Utility," Poster presented at International AIDS Conference, Barcelona, (Jul. 7-12, 2002).

HIV INTEGRASE INHIBITORS, PHARMACEUTICAL COMPOSITIONS AND METHODS FOR THEIR USE

This is a divisional application of U.S. patent application Ser. No. 10/765,227, filed Jan. 26, 2004, now U.S. Pat. No. 7,001,912, issued Feb. 21, 2006 which claims priority to U.S. patent application Ser. No. 60/443,223, filed Jan. 27, 2003, both of which are hereby incorporated by reference in their entirety.

FIELD OF THE INVENTION

The present invention is directed to beta-carboline hydroxamic acid compounds and pharmaceutically acceptable salts, pharmaceutically acceptable prodrugs, and pharmaceutically acceptable metabolites thereof, their synthesis, and their use as modulators or inhibitors of the human immunodeficiency virus ("HIV") Integrase enzyme. The compounds of the present invention are useful for modulating (e.g. inhibiting) an enzyme activity of HIV Integrase enzyme and for treating diseases or conditions mediated by HIV, such as for example, acquired immunodeficiency syndrome ("AIDS"), and AIDS related complex ("ARC").

BACKGROUND OF THE INVENTION

The retrovirus designated "human immunodeficiency virus" or "HIV" is the etiological agent of a complex disease that progressively destroys the immune system. The disease is known as acquired immune deficiency syndrome or AIDS. AIDS and other HIV-caused diseases are difficult to treat due to the ability of HIV to rapidly replicate, mutate and acquire resistance to drugs. To attempt to slow the spread of the virus after infection, treatment of AIDS and other HIV-caused diseases has focused on inhibiting HIV replication.

Since HIV is a retrovirus, and thus, encodes a positive-sense RNA strand, its mechanism of replication is based on the conversion of viral RNA to viral DNA, and subsequent insertion of the viral DNA into the host cell genome. HIV replication relies on three constitutive HIV encoded enzymes: reverse transcriptase (RT), protease and integrase.

Upon infection with HIV, the retroviral core particles bind to specific cellular receptors and gain entry into the host cell cytoplasm. Once inside the cytoplasm, viral RT catalyzes the reverse transcription of viral ssRNA to form viral RNA-DNA hybrids. The RNA strand from the hybrid is then partially degraded and a second DNA strand is synthesized resulting in viral dsDNA. Integrase, aided by viral and cellular proteins, then transports the viral dsDNA into the host cell nucleus as a component of the pre-integration complex (PIC). In addition, integrase provides the permanent attachment, i.e., integration, of the viral dsDNA to the host cell genome which, in turn, provides viral access to the host cellular machinery for gene expression. Following integration, transcription and translation produce viral precursor proteins. Protease then cleaves the viral precursor proteins into viral proteins, which, after additional processing, are released from the host cell as newly infectious HIV particles.

A key step in HIV replication, insertion of the viral dsDNA into the host cell genome, is believed to be mediated by integrase in at least three, and possibly, four, steps: (1) assembly of proviral DNA; (2) 3'-end processing causing assembly of the PIC; (3) 3'-end joining or DNA strand transfer, i.e., integration; and (4) gap filling, a repair function. See, e.g., Goldgur, Y. et al., *PNAS* 96(23): 13040–13043 (November 1999); Sayasith, K. et al., *Expert Opin. Ther. Targets* 5(4): 443–464 (2001); Young, S. D., *Curr. Opin. Drug Disc. & Devel.* 4(4): 402–410 (2001); Wai, J. S. et al., *J. Med. Chem.* 43(26): 4923–4926 (2000); Debyser, Z. et al., *Assays for the Evaluation of HIV-1 Integrase Inhibitors*, from *Methods in Molecular Biology* 160: 139–155, Schein, C. H. (ed.), Humana Press Inc., Totowa, N.J. (2001); and Hazuda, D. et al., *Drug Design and Disc.* 13: 17–24 (1997).

In the first step, integrase forms a stable complex with the viral long terminal repeat (LTR) regions. Once the complex is formed, integrase then performs an endonucleolytic processing step whereby the terminal GT dinucleotides of the 3' ends (immediately downstream from a conserved CA dinucleotide) of both DNA strands are cleaved. The processed DNA/integrase complex (the PIC) then translocates across the nuclear membrane. Once inside the host cell nucleus, integrase performs the third step, 3'-end joining, whereby a cut is made in the host cell DNA to covalently join the processed 3'-ends of the viral processed DNA during two transesterification reactions. In the fourth step, cellular enzymes repair the resultant gap at the site of viral DNA insertion. The enzymes, if any, employed in the repair process have not been accurately identified. Sayasith, K. et al., *Expert Opin. Ther. Targets* 5(4): 443–464 (2001). Thus, the role that integrase plays in the gap filling function is not known.

It is clear that the role that integrase plays in the integration of the viral DNA into the host cell genome occurs through well-ordered reactions directed by various viral and cellular factors. This knowledge provides a variety of opportunities to block the essential step of integration (and the essential enzyme integrase) in the HIV life cycle.

Currently, AIDS and other HIV-caused disease are treated with an "HIV cocktail" containing multiple drugs including RT and protease inhibitors. However, numerous side effects and the rapid emergence of drug resistance limit the ability of the RT and protease inhibitors to safely and effectively treat AIDS and other HIV-caused diseases. In view of the shortcomings of RT and protease inhibitors, there is a need for another mechanism through which HIV replication can be inhibited. Integration, and thus integrase, a virally encoded enzyme with no mammalian counterpart, is a logical alternative. See, e.g., Wai, J. S. et al., *J. Med. Chem.* 43:4923–4926 (2000); Grobler, J. et al., *PNAS* 99: 6661–6666 (2002); Pais, G. C. G. et al., *J. Med. Chem.* 45: 3184–3194 (2002); Young, S. D., *Curr. Opin. Drug Disc. & Devel.* 4(4): 402–410 (2001); Godwin, C. G. et al., *J. Med. Chem.* 45: 3184–3194 (2002); Young, S. D. et al., "L-870, 810: Discovery of a Potent HIV Integrase Inhibitor with Potential Clinical Utility," Poster presented at the XIV International AIDS Conference, Barcelona (Jul. 7–12, 2002); and WO 02/070491.

It has been suggested that for an integrase inhibitor to function, it should inhibit the strand transfer integrase function. See, e.g., Young, S. D., *Curr. Opin. Drug Disc. & Devel.* 4(4): 402–410 (2001). Thus, there is a need for HIV inhibitors, specifically, integrase inhibitors, and, more specifically, strand transfer inhibitors, to treat AIDS and other HIV-caused diseases. The inventive agents disclosed herein are novel, potent and selective HIV-integrase inhibitors, and, more specifically, strand transfer inhibitors, with high antiviral activity and low toxicity.

The references made to published documents throughout this application more fully describe the state of the art to which this invention pertains. The disclosures of these references are hereby incorporated by reference in their entireties.

SUMMARY OF THE INVENTION

The invention is directed to compounds represented by Formula I:

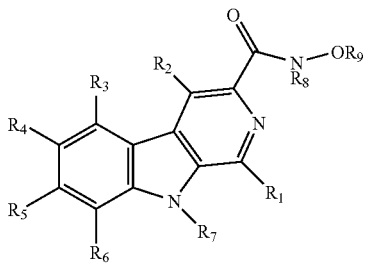

wherein:
  $R_1$, $R_2$, $R_3$, $R_4$, $R_5$, $R_6$ independently are selected from the group consisting of: hydrogen; halogen; and a lower alkyl, lower alkoxy alkyl, lower alkenyl, lower alkynyl, $OR_c$, and $N(R_c)_2$ group, unsubstituted or substituted with one or more halogens, where $R_c$ is hydrogen; oxygen; or an unsubstituted lower alkyl, unsubstituted lower alkenyl, or unsubstituted lower alkynyl group;
  $R_7$ is a lower alkyl, lower alkenyl, lower alkynyl, or —O—, unsubstituted or substituted with one or more substituents independently selected from the group consisting of:
    hydrogen; halogens; a lower alkyl, lower alkenyl, lower alkynyl, aryl, cycloalkyl, heterocycloalkyl, and heteroaryl group; and —O—, unsubstituted or substituted with one or more substituents independently selected from the group consisting of:
      halogens; hydrogen; and a lower alkyl, lower alkenyl, lower alkynyl, aryl, cycloalkyl, heterocycloalkyl, and heteroaryl group, unsubstituted or substituted with one or more halogens;
  $R_8$ and $R_9$ independently are selected from the group consisting of: hydrogen; and an alkyl, alkenyl, and alkynyl group, unsubstituted or substituted with one or more substituents independently selected from the group consisting of:
    halogens; and an aryl, cycloalkyl, heterocycloalkyl, and heteroaryl group, unsubstituted or substituted with one or more substituents independently selected from the group consisting of:
      halogens; and an unsubstituted lower alkyl, unsubstituted lower alkenyl, and unsubstituted lower alkynyl group; and
  $R_2$ and $R_8$ together with the N to which $R_8$ is attached cyclize to form the following compound represented by the Formula Ib:

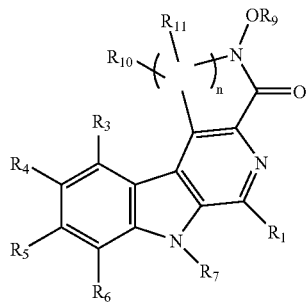

wherein $R_{10}$ and $R_{11}$ are each independently:
  hydrogen; halogen; a lower alkyl, lower alkenyl, lower alkynyl, $OR_c$, or $N(R_c)_2$ group, unsubstituted or substituted with one or more substituents independently selected from the group consisting of:
    halogens; and an aryl, cycloalkyl, heterocycloalkyl, and heteroaryl group, unsubstituted or substituted with one or more substituents independently selected from the group consisting of:
      halogens; and an unsubstituted lower alkyl, unsubstituted lower alkenyl, and unsubstituted lower alkynyl group;
  where $R_c$ is halogen; hydrogen; oxygen; or an unsubstituted lower alkyl, unsubstituted lower alkenyl, or unsubstituted lower alkynyl group; and
  n is 1, 2 or 3.

The present invention also provides compounds of Formula (I),

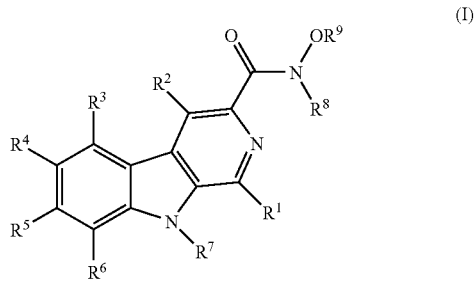

wherein:
  $R_1$, $R_2$, $R_3$, $R_4$, $R_5$, and $R_6$ are independently selected from hydrogen, halogen, $C_1$–$C_6$ alkyl, alkoxy $C_1$–$C_6$ alkyl, $C_2$–$C_6$ alkenyl, $C_2$–$C_6$ alkynyl, —$OR_c$, —$NO_2$, and —$N(R_c)_2$;
  each $R_c$ is independently selected from hydrogen, $C_1$–$C_6$ alkyl, $C_2$–$C_6$ alkenyl, and $C_2$–$C_6$ alkynyl;
  $R_7$ is $C_1$–$C_6$ alkyl, $C_2$–$C_6$ alkenyl, or $C_2$–$C_6$ alkynyl, all of which are optionally substituted by one or more substituents independently selected from halogen, $C_1$–$C_6$ alkyl, $C_2$–$C_6$ alkenyl, $C_2$–$C_6$ alkynyl, aryl, cycloalkyl, heterocycloalkyl, and heteroaryl, wherein said aryl, cycloalkyl, and heterocycloalkyl are optionally substituted with one or more substituents independently selected from halogen, $C_1$–$C_6$ alkyl, $C_2$–$C_6$ alkenyl, and $C_2$–$C_6$ alkynyl;

$R_8$ and $R_9$ are independently selected from hydrogen, $C_1$–$C_6$ alkyl, $C_2$–$C_6$ alkenyl, and $C_2$–$C_6$ alkynyl, wherein said alkyl, alkenyl, and alkynyl are optionally substituted with one or more substituents independently selected from halogen, aryl, cycloalkyl, heterocycloalkyl, and heteroaryl group, wherein said aryl, cycloalkyl, and heterocycloalkyl are optionally substituted with one or more substituents independently selected from halogen, $C_1$–$C_6$ alkyl, $C_2$–$C_6$ alkenyl, and $C_2$–$C_6$ alkynyl; and pharmaceutically acceptable salts and solvates thereof.

In another aspect of the present invention are provided compounds of Formula (I), wherein:

$R_1$, $R_2$, $R_3$, $R_4$, $R_5$, and $R_6$ are independently selected from hydrogen, —N($R_c$)$_2$, and —NO$_2$; and $R_c$ is selected from hydrogen, $C_1$–$C_6$ alkyl, $C_2$–$C_6$ alkenyl, and $C_2$–$C_6$ alkynyl; and pharmaceutically acceptable salts and solvates thereof.

In yet another aspect of the present invention are provided compounds of formula (I) wherein $R_7$ is $C_1$–$C_6$ alkyl, optionally substituted with aryl, cycloalkyl, heterocycloalkyl, and heteroaryl, wherein said aryl, cycloalkyl, heterocycloalkyl, and heteroaryl are optionally substituted with at least one substituent selected from halogen, $C_1$–$C_6$ alkyl, $C_2$–$C_6$ alkenyl, and $C_2$–$C_6$ alkynyl; and pharmaceutically acceptable salts and solvates thereof.

In still another aspect of the present invention are provided compounds of formula (I), wherein $R_8$ and $R_9$ are independently selected from hydrogen and $C_1$–$C_6$ alkyl, wherein said alkyl group is optionally substituted with aryl, and wherein said aryl is optionally substituted with at least one substituent selected from halogen and $C_1$–$C_6$ alkyl; and pharmaceutically acceptable salts and solvates thereof.

In still a further aspect of the present invention are provided compound of formula (I), wherein:

$R_1$, $R_2$, $R_3$, $R_4$, $R_5$, and $R_6$ are independently selected from hydrogen and —N($R_c$)$_2$;

$R_c$ is hydrogen, $C_1$–$C_6$ alkyl, $C_2$–$C_6$ alkenyl, and $C_2$–$C_6$ alkynyl;

$R_7$ is $C_1$–$C_6$ alkyl, optionally substituted with at least one substituent selected from aryl, cycloalkyl, heterocycloalkyl, and heteroaryl, wherein said aryl, cycloalkyl, heterocycloalkyl, and heteroaryl are optionally substituted with at least one substituent selected from halogen, $C_1$–$C_6$ alkyl, $C_2$–$C_6$ alkenyl, and $C_2$–$C_6$ alkynyl;

$R_8$ and $R_9$ are independently selected from hydrogen and $C_1$–$C_6$ alkyl, wherein said alkyl is optionally substituted with at least one substituent selected from aryl group, wherein said aryl is optionally substituted with at least one substituent selected from halogen, and $C_1$–$C_6$ alkyl; and pharmaceutically acceptable salts and solvates thereof.

In yet another aspect of the invention are provided compounds of formula (I), wherein:

$R_1$, $R_2$, $R_3$, $R_4$, $R_5$, $R_6$ are independently selected from hydrogen, —NH$_2$; and —NO$_2$;

$R_7$ is 4-fluorobenzyl, (5-chlorothien-2-yl)methyl, 3-chloro-2-fluorobenzyl, benzyl, 4-methylbenzyl, 2,4-difluorobenzyl, 3-chloro-2,6-difluorobenzyl, or 3-chlorobenzyl; and $R_8$ and $R_9$ are independently selected from hydrogen, methyl, and benzyl; and pharmaceutically acceptable salts and solvates thereof.

Another aspect of the present invention provides compounds of formula (I), wherein:

$R_1$, $R_2$, $R_3$, $R_4$, $R_5$ and $R_6$ are hydrogen;

$R_7$ is —CH$_2$phenyl, wherein said phenyl is substituted with at least one substitutent chosen from fluorine and chlorine;

$R_8$ is hydrogen or —CH$_3$;

$R_9$ is hydrogen or —CH$_3$; and pharmaceutically acceptable salts and solvates thereof.

In still another aspect of the present invention are provided compounds of formula (I), wherein:

$R_1$, $R_2$, $R_3$, $R_5$ and $R_6$ are hydrogen;

$R_4$ is —NO$_2$ or —NH$_2$;

$R_7$ is —CH$_2$phenyl, wherein said phenyl is substituted with at least one subtitutent chosen from fluorine and chlorine;

$R_8$ is hydrogen or —CH$_3$;

$R_9$ is hydrogen or —CH$_3$; and pharmaceutically acceptable salts and solvates thereof.

In yet another aspect of the present invention are provided compounds of formula (I), wherein:

$R_1$, $R_2$, $R_3$, $R_4$, $R_5$ and $R_6$ are hydrogen;

$R_7$ is —CH$_2$phenyl, wherein said phenyl is substituted with at least one subtitutent chosen from fluorine and chlorine;

$R_8$ and $R_9$ are hydrogen; and pharmaceutically acceptable salts and solvates thereof.

Another aspect of the present invention provides compounds of formula (I), wherein:

$R_1$, $R_2$, $R_3$, $R_4$, $R_5$ and $R_6$ are hydrogen;

$R_7$ is —CH$_2$phenyl, wherein said phenyl is substituted with at least one subtitutent chosen from fluorine and chlorine;

$R_8$ and $R_9$ are —CH$_3$; and pharmaceutically acceptable salts and solvates thereof.

Another aspect of the present invention provides compounds of formula (I), wherein:

$R_1$, $R_2$, $R_3$, $R_4$, $R_5$ and $R_6$ are hydrogen;

$R_7$ is —CH$_2$phenyl, wherein said phenyl is substituted with at least one subtitutent chosen from fluorine and chlorine;

$R_8$ is hydrogen;

$R_9$ is —CH$_3$; and pharmaceutically acceptable salts and solvates thereof.

Another aspect of the present invention provides compounds of formula (I), wherein:

$R_1$, $R_2$, $R_3$, $R_4$, $R_5$ and $R_6$ are hydrogen;

$R_7$ is —CH$_2$phenyl, wherein said phenyl is substituted with at least one subtitutent chosen from fluorine and chlorine;

$R_8$ is —CH$_3$;

$R_9$ is hydrogen; and pharmaceutically acceptable salts and solvates thereof.

In another aspect of the present invention, the compounds of formula (I) are selected from 9-(4-Fluorobenzyl)-N-hydroxy-9H-β-carboline-3-carboxamide; 9-[(5-Chlorothien-2-yl)methyl]-N-hydroxy-9H-β-carboline-3-carboxamide; 9-(3-Chloro-2-fluorobenzyl)-N-hydroxy-9H-β-carboline-3-carboxamide; 9-Benzyl-N-hydroxy-9H-β-carboline-3-carboxamide; 9-(4-Methylbenzyl)-N-Hydroxy-9H-β-carboline-3-carboxamide; 9-(2,4-Difluorobenzyl)-N-hydroxy-9H-β-carboline-3-carboxamide; 9-(3-Chloro-2,6-difluorobenzyl)-N-hydroxy-9H-β-carboline-3-carboxamide; 6-Amino-9-(3-chlorobenzyl)-N-hydroxy-9H-β-carboline-3-carboxamide; 9-(3-Chloro-2,6-difluorobenzyl)-N-methoxy-9H-β-carboline-3-carboxamide; N-(Benzyloxy)-9-(3-chloro-2,6-difluorobenzyl)-9H-β-carboline-3-carboxamide; 9-(3-Chloro-2,6-difluorobenzyl)-N-hydroxy-N-methyl-9H-β-carboline-3-carboxamide; N-Benzyl-9-(3-chloro-2,6-difluorobenzyl)-N-hydroxy-9H-β-carboline-3-carboxamide; 9-(4-fluorobenzyl)-N-hydroxy-N-methyl-9H-β-carboline-3-carboxamide; and pharmaceutically acceptable salts and solvates thereof.

In another aspect of the present invention are provided compounds of formula (Ib),

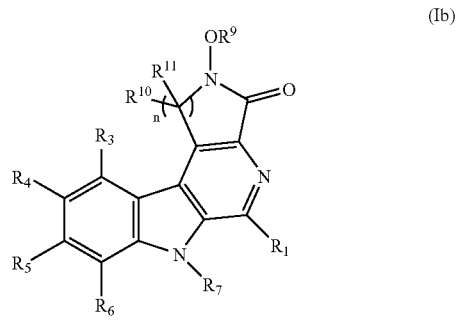

wherein:
$R_1$, $R_3$, $R_4$, $R_5$, and $R_6$ are independently selected from hydrogen, halogen, $C_1$–$C_6$ alkyl, alkoxy $C_1$–$C_6$ alkyl, $C_2$–$C_6$ alkenyl, $C_2$–$C_6$ alkynyl, —$OR_c$, —$NO_2$, and —$N(R_c)_2$;
each $R_c$ is independently selected from hydrogen, $C_1$–$C_6$ alkyl, $C_2$–$C_6$ alkenyl, and $C_2$–$C_6$ alkynyl;
$R_7$ is $C_1$–$C_6$ alkyl, $C_2$–$C_6$ alkenyl, or $C_2$–$C_6$ alkynyl, all of which are optionally substituted by one or more substituents independently selected from halogen, $C_1$–$C_6$ alkyl, $C_2$–$C_6$ alkenyl, $C_2$–$C_6$ alkynyl, aryl, cycloalkyl, heterocycloalkyl, and heteroaryl, wherein said aryl, cycloalkyl, and heterocycloalkyl are optionally substituted with one or more substituents independently selected from halogen, $C_1$–$C_6$ alkyl, $C_2$–$C_6$ alkenyl, and $C_2$–$C_6$ alkynyl;
$R_9$ is independently selected from hydrogen, $C_1$–$C_6$ alkyl, $C_2$–$C_6$ alkenyl, and $C_2$–$C_6$ alkynyl, wherein said alkyl, alkenyl, and alkynyl are optionally substituted with one or more substituents independently selected from halogen, aryl, cycloalkyl, heterocycloalkyl, and heteroaryl group, wherein said aryl, cycloalkyl, and heterocycloalkyl are optionally substituted with one or more substituents independently selected from halogen, $C_1$–$C_6$ alkyl, $C_2$–$C_6$ alkenyl, and $C_2$–$C_6$ alkynyl;
each $R_{10}$ and $R_{11}$ are independently selected from hydrogen, halogen, $C_1$–$C_6$ alkyl, $C_2$–$C_6$ alkenyl, and $C_2$–$C_6$ alkynyl, —$OR_c$, or —$N(R_c)_2$ group, wherein said alkyl, alkenyl, and alkynyl are optionally substituted by one or more substituents selected from halogen, aryl, cycloalkyl, heterocycloalkyl, and heteroaryl group, wherein said aryl, cycloalkyl, heterocycloalkyl, and heteroaryl are optionally substituted with at least one substitutent independently selected from halogen, $C_1$–$C_6$ alkyl, $C_2$–$C_6$ alkenyl, and $C_2$–$C_6$ alkynyl;
n is 1, 2 or 3; and
pharmaceutically acceptable salts and solvates thereof.

In addition to compounds of formula (I) and (Ib), the invention is also directed to pharmaceutically acceptable salts, pharmaceutically acceptable prodrugs, and pharmaceutically active metabolites of such compounds, and pharmaceutically acceptable salts of such metabolites. Such compounds, salts, prodrugs and metabolites are at times collectively referred to herein as "HIV Integrase agents."

The invention also relates to pharmaceutical compositions, each comprising a therapeutically effective amount of at least one HIV Integrase agent according to the invention and a pharmaceutically acceptable carrier, diluent, or vehicle therefore.

Additionally, the invention is directed to methods of inhibiting or modulating an enzyme activity of human immunodeficiency virus (HIV) integrase, comprising contacting said enzyme with an effective amount of at least one HIV Integrase agent of the invention.

In another aspect, the invention is directed to methods of treating a disease or condition mediated by human immunodeficiency virus (HIV) integrase enzyme, comprising administering to a mammal in need of such treatment a therapeutically effective amount of at least one HIV Integrase agent of the invention. The disease or condition may be, for example, acquired immunodeficiency syndrome (AIDS) or AIDS related complex (ARC).

In a further aspect of the present invention are provided methods for inhibiting the replication of human immunodeficiency virus (HIV) in a mammal, comprising administering a human immunodeficiency virus inhibiting amount of a compound of formula (I) or (Ib), or a pharmaceutically acceptable salt or solvate thereof, to said mammal.

In another aspect of the present invention are provided methods of inhibiting the activity of the HIV integrase enzyme, comprising contacting said enzyme with a HIV integrase enzyme-inhibiting amount of a compound of formula (I) or (Ib), or a pharmaceutically acceptable salt or solvate thereof. Also provided in the present invention are those methods of inhibiting the activity of the HIV integrase enzyme, wherein the enzyme is found in a mammal.

A further aspect of the present invention provides a medicament, comprising a compound of formula (I) or (Ib), or a pharmaceutically acceptable salt or solvate thereof, for the treatment of a disease or condition mediated by human immunodeficiency virus (HIV) integrase enzyme.

As used herein, the terms "comprising" and "including" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by "I"), ethyl (Et), n-propyl, isopropyl, butyl, isobutyl, sec-butyl, tert-butyl (tBu), pentyl, isopentyl, neo-pentyl, hexyl, isohexyl, and the like.

The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary alkyl amines, alkyl sulfides, and the like.

The term "alkenyl" refers to a straight- or branched-chain alkenyl group having from 2 to 12 carbon atoms in the chain. Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. Illustrative alkynyl groups include prop-2-ynyl, but-2-ynyl, but-3-ynyl, 2-methylbut-2-ynyl, hex-2-ynyl, and the like.

The terms "lower alkyl", "lower alkenyl", and "lower alkynyl" refer, respectively, to an alkyl, alkenyl, and alkynyl group having from one (1) to six (6) carbon atoms in the chain.

The term "haloalkyl" refers to a straight- or branched-chain alkyl, alkenyl or alkynyl group having from 2–12 carbon atoms in the chain and where one or more hydrogens is replaced with a halogen. Illustrative haloalkyl groups include trifluoromethyl, 2-bromopropyl, 3-chlorohexyl, 1-iodo-isobutyl, and the like.

The term "aryl" (Ar) refers to a monocyclic, or fused or spiro polycyclic, aromatic carbocycle (ring structure having ring atoms that are all carbon) having from 3 to 12 ring atoms per ring. Illustrative examples of aryl groups include the following moieties:

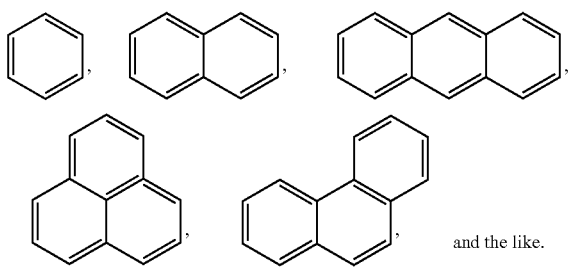

and the like.

The term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

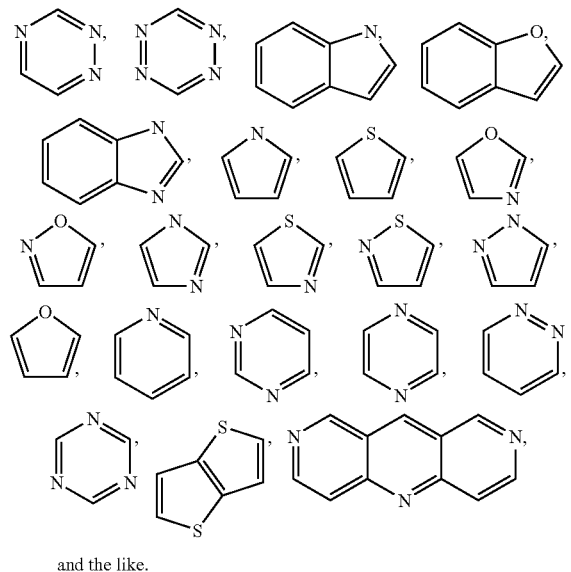

and the like.

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

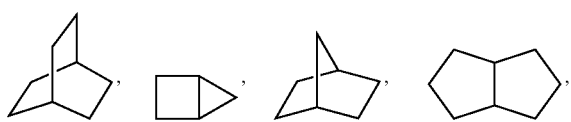

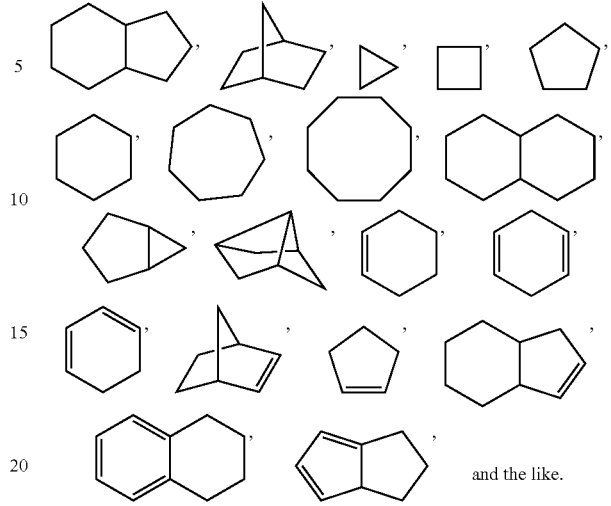

and the like.

The term "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

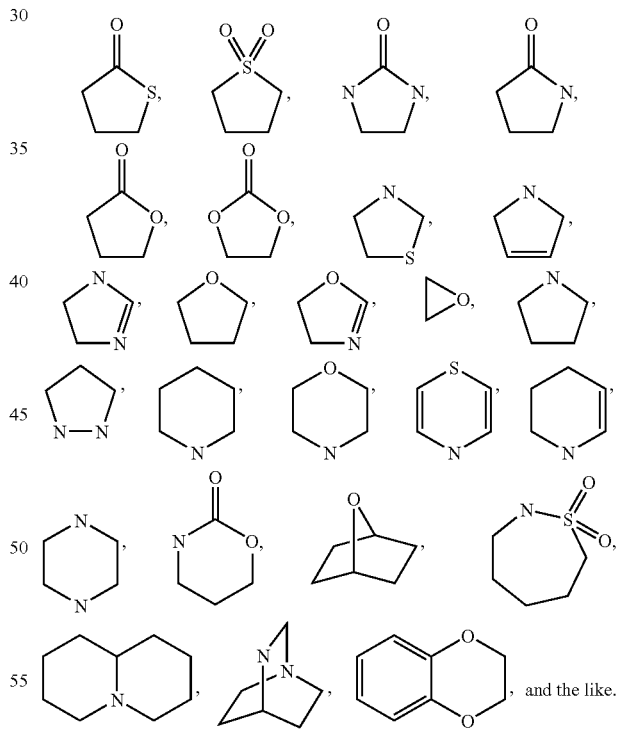

and the like.

The term "halogen(s)" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents.

The term "optionally substituted" means that the specified group is unsubstituted or substituted by one or more substituents.

The term "pharmaceutically acceptable salts" refers to salt forms that are pharmacologically acceptable and substantially non-toxic to the subject being administered the HIV Integrase agent.

A "therapeutically effective amount" is intended to mean that amount of a compound that, when administered to a mammal in need of such treatment, is sufficient to effect treatment, as defined herein. Thus, e.g., a therapeutically effective amount of a compound of the Formula I, salt, active metabolite or prodrug thereof, is a quantity sufficient to modulate or inhibit the activity of HIV Integrase such that a disease condition that is mediated by activity is reduced or alleviated.

The terms "treat", "treating", and "treatment" refer to any treatment of a HIV Integrase mediated disease or condition in a mammal, particularly a human, and include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition.

The term "human immunodeficiency virus-inhibiting amount," as used herein, refers to the amount of a compound of the present invention, or a pharmaceutically acceptable salt of solvate thereof, required to inhibit replication of the human immunodeficiency virus (HIV) in vivo, such as in a mammal, or in vitro. The amount of such compounds required to cause such inhibition can be determined without undue experimentation using methods known to those of ordinary skill in the art and those described herein.

The term, "HIV integrase enzyme-inhibiting amount," as used herein refers to the amount of a compound of the present invention, or a pharmaceutically acceptable salt or solvate thereof, required to descrease the activity of the HIV integrase enzyme either in vivo, such as in a mammal, or in vitro. Such inhibition can take place by contacting the HIV integrase enzyme with a compound of the present invention, or a pharmaceutically acceptable salt or solvate thereof. Such inhibition may take place by the compound of the present invention binding directly to the HIV integrase enzyme. In addition, the activity of the HIV integrase enzyme may be decreased in the presence of a compound of the present invention when such direct binding between the enzyme and the compound does not take place. Furthermore, such inhibition may be competitive, non-competitive, or uncompetitive. Such inhibition may be determined using in vitro or in vivo systems, or a combination of both, using methods known to those of ordinary skill in the art.

The term, "compound of the present invention" refers to compounds of formula (I) or (Ib), or pharmaceutically acceptable salts or solvates thereof.

DETAILED DESCRIPTION

The compounds of the present invention are useful for modulating or inhibiting HIV Integrase enzyme. More particularly, the compounds of the present invention are useful as modulators or inhibitors of HIV Integrase activity, and thus are useful for the prevention and/or treatment of HIV mediated diseases or conditions (e.g., AIDS, and ARC), alone or in combination with other known antiviral agents.

The compounds of the present invention may have asymmetric carbon atoms. The carbon-carbon bonds in the compounds of the present invention may be depicted herein using a solid line ($\delta$), a solid wedge (━■), or a dotted wedge (·····II). The use of a solid line to depict bonds to asymmetric carbon atoms is meant to indicate that all possible stereoisomers at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Individual enantiomers of the compounds of the present invention can be designated as either the (R)- or (S)-enantiomer using conventional naming protocols known to those of ordinary skill in the art and as described in E. L. Eliel et al., *Stereochemistry of Organic Compounds*, Wiley: New York, 1994. Furthermore, when a compound of the present invention contains more than one chiral carbon atom, the stereochemistry of the individual carbon atoms may be assigned as of either the (R)- or (S)-configuration according to methods known to those of ordinary skill in the art and as described in E. L. Eliel et al., *Stereochemistry of Organic Compounds*, Wiley: New York, 1994.

Solutions of individual stereoisomeric compounds of the present invention may rotate plane-polarized light. The use of either a "(+)" or "(−)" symbol in the name of a compound of the invention indicates that a solution of a particular stereoisomer rotates plane-polarized light in the (+) or (−) direction, as measured using techniques known to those of ordinary skill in the art and as described in E. L. Eliel et al., *Stereochemistry of Organic Compounds*, Wiley: New York, 1994.

Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. Other methods of separating individual diastereomeric compounds are described in E. L. Eliel et al., *Stereochemistry of Organic Compounds*, Wiley: New York, 1994. All such isomers, including enantiomeric mixtures, diastereomeric mixtures, and pure enantiomers are considered part of the present invention.

Alternatively, individual stereoisomeric compounds of the present invention may be prepared in enantiomerically enriched form by asymmetric synthesis, followed by purification as described above if necessary. Asymmetric synthesis may be performed using techniques known to those of ordinary skill in the art, such as the use of asymmetric starting materials that are commercially available or readily prepared using methods known to those of ordinary skill in the art, the use of asymmetric auxiliaries that may be removed at the completion of the synthesis, or the resolution of intermediate compounds using enzymatic methods. Other methods of preparing enantiomerically pure compounds are described in E. L. Eliel et al., *Stereochemistry of Organic Compounds*, Wiley: New York, 1994. The choice of which method is used will depend on factors that include, but are not limited to, the availability of starting materials, the relative efficiency of a method, and whether such methods are useful for the compounds of the invention containing particular functional groups. Such choices are within the knowledge of one of ordinary skill in the art.

When the compounds of the present invention contain asymmetric carbon atoms, the compounds, pharmaceutically acceptable salts or solvates may exist as single stereoisomers, racemates, and/or mixtures of enantiomers and/or diastereomers. All such single stereoisomers, racemates, and mixtures thereof are intended to be within the scope of the present invention.

It is understood that while a compound may exhibit the phenomenon of tautomerism, the formula drawings within this specification expressly depict only one of the possible tautomeric forms. It is therefore to be understood that a formula is intended to represent any tautomeric form of the depicted compound and is not to be limited merely to a specific compound form depicted by the structural formula.

It is also understood that a compound of the present invention may exist as an "E" or "Z" configurational isomer, or a mixture of E and Z isomers. It is therefore to be understood that a formula is intended to represent any configurational form of the depicted compound and is not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. In one embodiment, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, formulae (I) and (Ib) are intended to cover, where applicable, solvated as well as unsolvated forms of the compounds. Thus, each formula includes compounds having the indicated structure, including the hydrated as well as the non-hydrated forms.

In addition to compounds of the present invention, the HIV Integrase agents of the invention include pharmaceutically acceptable salts, prodrugs, and active metabolites of such compounds, and pharmaceutically acceptable salts of such metabolites. A "pharmaceutically acceptable prodrug" is a compound that may be converted under physiological conditions or by solvolysis to the specified compound or to a pharmaceutically acceptable salt of such compound. A "pharmaceutically active metabolite" is a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86(7), 765–767 (1997); Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); Larsen, *Design and Application of Prodrugs, Drug Design and Development* (Krogsgaard-Larsen et al. eds., Harwood Academic Publishers, 1991); Dear et al., *J. Chromatogr. B*, 748, 281–293 (2000); Spraul et al., *J. Pharmaceutical & Biomedical Analysis*, 10(8), 601–605 (1992); and Prox et al., *Xenobiol.*, 3(2), 103–112 (1992).

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

A "solvate" is intended to mean a pharmaceutically acceptable solvate form of a specified compound that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof.

A "pharmaceutically acceptable salt" is intended to mean a salt that retains the biological effectiveness of the free acids and bases of the specified derivative, containing pharmacologically acceptable anions, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

It is understood by those of ordinary skill in the art that the compounds of the present invention, or their pharmaceutically acceptable salts or solvates, may exist in different polymorph or crystal forms, all of which are intended to be within the scope of the present invention and specified formulas. In addition, the compounds of the present invention, and their pharmaceutically acceptable salts and solvates, may exist as tautomers, all of which are intended to be within the broad scope of the present invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The HIV Integrase agents of the invention may be formulated into pharmaceutical compositions as described below in any pharmaceutical form recognizable to the skilled artisan as being suitable. Pharmaceutical compositions of the invention comprise a therapeutically effective amount of at least one compound of Formula I and an inert, pharmaceutically acceptable carrier or diluent.

To treat or prevent diseases or conditions mediated by HIV, a pharmaceutical composition of the invention is administered in a suitable formulation prepared by combining a therapeutically effective amount (i.e., an HIV Integrase modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl disterate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration chosen. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insulator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used. Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals. Administration of prodrugs may be dosed at weight levels that are chemically equivalent to the weight levels of the fully active compounds.

The compounds of the present invention may be administered in combination with an additional agent or agents for the treatment of a mammal, such as a human, that is suffering from an infection with the HIV virus, AIDS, AIDS-related complex (ARC), or any other disease or condition which is related to infection with the HIV virus. The agents that may be used in combination with the compounds of the present invention include, but are not limited to, those useful as HIV protease inhibitors, HIV reverse transcriptase inhibitors, non-nucleoside HIV reverse transcriptase inhibitors, inhibitors of HIV integrase, CCR5 inhibitors, HIV fusion inhibitors, compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compounds of the present invention include, but are not limited to, 141 W94 (amprenavir), CGP-73547, CGP-61755, DMP-450, nelfinavir, ritonavir, saquinavir (invirase), lopinavir, TMC-126, BMS-232632 (atazanavir), palinavir, GS-3333, KNI-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, TMC-114, DPC-681, DPC-684, fosamprenavir calcium (Lexiva), benzenesulfonamide derivatives disclosed in WO 03053435, R-944, Ro-03-34649, VX-385, GS-224338, OPT-TL3, PL-100, SM-309515, AG-148, DG-35-VIII, DMP-850, GW-5950X, KNI-1039, L-756423, LB-71262, LP-130, RS-344, SE-063, UIC-94-003, Vb-19038, A-77003, BMS-182193, BMS-186318, SM-309515, and JE-2147.

Compounds useful as inhibitors of the HIV reverse transcriptase enzyme that may be used in combination with the compounds of the present invention include, but are not limited to, abacavir (1592U89), FTC, GS-840, lamivudine (3TC), adefovir dipivoxil, beta-fluoro-ddA, ddC (dideoxycytidine, zalcitabine), ddI (dideoxyinsine, didanosine), stavudine (d4T), zidovudine (AZT), tenofovir, amdoxovir, SPD-754, SPD-756, racivir, reverset (DPC-817), MIV-210 (FLG), beta-L-Fd4C (ACH-126443), MIV-310 (alovudine, FLT), dOTC, DAPD, and emtricitabine.

Compounds useful as non-nucleoside inhibitors of the HIV reverse transcriptase enzyme include, but are not limited to, efavirenz, HBY-097, nevirapine, TMC-120 (dapivirine), TMC-125, delaviradine, DPC-083, DPC-961, TMC-120, capravirine, and tricyclic pyrimidinone derivatives as disclosed in WO 03062238.

Compounds useful as CCR5 inhibitors that may be used in combination with the compounds of the present invention include, but are not limited to, TAK-779, SC-351125, SCH-D, UK-427857, PRO-140, and GW-873140 (Ono-4128, AK-602).

Compounds useful as inhibitors of HIV integrase enzyme that may be used in combination with the compounds of the present invention include, but are not limited to, 1,5-naphthyridine-3-carboxamide derivatives disclosed in WO 03062204, compounds disclosed in WO 03047564, compounds disclosed in WO 03049690, and 5-hydroxypyrimidine-4-carboxamide derivatives disclosed in WO 03035076.

Fusion inhibitors for the treatment of HIV that may be used in combination with the compounds of the present invention include, but are not limited to, T20, T-1249, AMD-3100, and fused tricyclic compounds disclosed in JP 2003171381.

Other compounds that are useful inhibitors of HIV that may be used in combination with the compounds of the present invention include, but are not limited to, Soluble CD4, TNX-355, PRO-542, BMS-806, tenofovir disoproxil fumarate, and compounds disclosed in JP 2003119137.

Compounds useful in the treatment or management of infection from viruses other than HIV that may be used in combination with the compounds of the present invention include, but are not limited to, acyclovir, penciclovir, HPMPC, oxetanocin G, AL-721, cidofovir, cytomegalovirus immune globin, cytovene, ganciclovir, famciclovir, Isis 2922, KNI-272, valaciclovir, and virazole ribavirin.

Compounds that act as immunomodulators and may be used in combination with the compounds of the present invention include, but are not limited to, AD-439, AD-519, Alpha Interferon, AS-101, bropirimine, acemannan, CL246, 738, EL10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sactor, remune, rCD4, recombinant soluble human CD4, interferon alfa-2, SK&F106528, soluble T4 yhymopentin, tumor necrosis factor (TNF), tucaresol, recombinant human interferon beta, and interferon alfa n-3.

Anti-infectives that may be used in combination with the compounds of the present invention include, but are not limited to, clindamycin with primaquine, fluconazole, pastill, ornidyl, eflornithine pentamidine, spiramycin, intraconazole-R51211, trimetrexate, daunorubicin, recombinant human erythropoietin, recombinant human growth hormone, megestrol acetate, testerone, and total enteral nutrition.

Other compounds that may be used in combination with the compounds of the present invention include, but are not limited to, acmannan, ansamycin, LM 427, AR177, BMS-232623, BMS-234475, CI-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with compounds that act as inhibitors of metallo-matrix proteases, so-called MMP inhibitors.

The particular choice of an additional agent or agents will depend on a number of factors that include, but are not limited to, the condition of the mammal being treated, the particular condition or conditions being treated, the identity of the compound or compounds of the present invention and the additional agent or agents, and the identity of any additional compounds that are being used to treat the mammal. The particular choice of the compound or compounds of the invention and the additional agent or agents is within the knowledge of one of ordinary skill in the art.

The compounds of the present invention may be administered in combination with any of the above additional agents for the treatment of a mammal, such as a human, that is suffering from an infection with the HIV virus, AIDS, AIDS-related complex (ARC), or any other disease or condition which is related to infection with the HIV virus. Such a combination may be administered to a mammal such that a compound or compounds of the present invention are present in the same formulation as the additional agents described above. Alternatively, such a combination may be administered to a mammal suffering from infection with the HIV virus such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

Additionally, the compounds of the present invention may be administered to a mammal, such as a human, in combination with an additional agent that has the effect of increasing the exposure of the mammal to a compound of the invention. The term "exposure," as used herein, refers to the concentration of a compound of the invention in the plasma of a mammal as measured over a period of time. The exposure of a mammal to a particular compound can be measured by administering a compound of the invention to a mammal in an appropriate form, withdrawing plasma samples at predetermined times, and measuring the amount of a compound of the invention in the plasma using an appropriate analytical technique, such as liquid chromatography or liquid chromatography/mass spectroscopy. The amount of a compound of the invention present in the plasma at a certain time is determined and the concentration and time data from all the samples are plotted to afford a curve. The area under this curve is calculated and affords the exposure of the mammal to the compound. The terms "exposure," "area under the curve," and "area under the concentration/time curve" are intended to have the same meaning and may be used interchangeably throughout.

Among the agents that may be used to increase the exposure of a mammal to a compound of the present invention are those that can as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include, but are not limited to, ritonavir.

Such a combination may be administered to a mammal such that a compound or compounds of the present invention are present in the same formulation as the additional agents described above. Alternatively, such a combination may be administered such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

Several different assay formats are available to measure integrase-mediated integration of viral DNA into target (or host) DNA and thus, identify compounds that modulate (e.g., inhibit) integrase activity. In general, for example, ligand-binding assays may be used to determine interaction with an enzyme of interest. When binding is of interest, a labeled enzyme may be used, wherein the label is a fluorescer, radioisotope, or the like, which registers a quantifiable change upon binding to the enzyme. Alternatively, the skilled artisan may employ an antibody for binding to the enzyme, wherein the antibody is labeled allowing for amplification of the signal. Thus, binding may be determined through direct measurement of ligand binding to an enzyme. In addition, binding may be determined by competitive displacement of a ligand bound to an enzyme, wherein the ligand is labeled with a detectable label. When inhibitory activity is of interest, an intact organism or cell may be studied, and the change in an organismic or cellular function in response to the binding of the inhibitory compound may be measured. Alternatively, cellular response can be determined microscopically by monitoring viral induced syncytium-formation (HIV-1 syncytium-formation assays), for example. Thus, there are various in vitro and in vivo assays useful for measuring HIV integrase inhibitory activity. See, e.g., Lewin, S. R. et al., *Journal of Virology* 73(7): 6099–6103 (July 1999); Hansen, M. S. et al., *Nature Biotechnology* 17(6): 578–582 (June 1999); and Butler, S. L. et al., *Nature Medicine* 7(5): 631–634 (May 2001).

Exemplary specific assay formats used to measure integrase-mediated integration include, but are not limited to, ELISA, DELFIA® (PerkinElmer Life Sciences Inc. (Boston, Mass.)) and ORIGEN® (IGEN International, Inc. (Gaithersburg, Md.)) technologies. In addition, gel-based integration (detecting integration by measuring product formation with SDS-PAGE) and scintillation proximity assay (SPA) disintegration assays that use a single unit of double stranded-DNA (ds-DNA) may be used to monitor integrase activity.

In one embodiment of the invention, the preferred assay is an integrase strand-transfer SPA (stINTSPA) which uses SPA to specifically measure the strand-transfer mechanism of integrase in a homogenous assay scalable for miniaturization to allow high-throughput screening. The assay focuses on strand transfer and not on DNA binding and/or 3' processing. This sensitive and reproducible assay is capable of distinguishing non-specific interactions from true enzymatic function by forming 3' processed viral DNA/integrase complexes before the addition of target DNA. Such a formation creates a bias toward compound modulators (e.g., inhibitors) of strand-transfer and not toward compounds that inhibit integrase 3' processing or prevent the association of integrase with viral DNA. This bias renders the assay more specific than known assays. In addition, the homogenous nature of the assay reduces the number of steps required to run the assay since the wash steps of a heterogenous assay are not required.

The integrase strand-transfer SPA format consists of 2 DNA components that model viral DNA and target DNA. The model viral DNA (also known as donor DNA) is biotinylated ds-DNA preprocessed at the 3' end to provide a CA nucleotide base overhang at the 5' end of the duplex. The target DNA (also known as host DNA) is a random nucleotide sequence of ds-DNA generally containing [$^3$H]-thymidine nucleotides on both strands, preferably, at the 3' ends, to enable detection of the integrase strand-transfer reaction that occurs on both strands of target ds-DNA.

Integrase (created recombinantly or synthetically and preferably, purified) is pre-complexed to the viral DNA bound to a surface, such as for example, streptavidin-coated SPA beads. Generally, the integrase is pre-complexed in a batch process by combining and incubating diluted viral DNA with integrase and then removing unbound integrase. The preferred molar ratio of viral DNA:integrase is about 1:about 5. The integrase/viral DNA incubation is optional, however, the incubation does provide for an increased specificity index with an integrase/viral DNA incubation time of about 15 to about 30 minutes at room temperature or at about 37° C. The preferred incubation is at about room temperature for about 15 minutes.

The reaction is initiated by adding target DNA, in the absence or presence of a potential integrase modulator compound, to the integrase/viral DNA beads (for example) and allowed to run for about 20 to about 50 minutes (depending on the type of assay container employed), at about room temperature or about 37° C., preferably, at about 37° C. The assay is terminated by adding stop buffer to the integrase reaction mixture. Components of the stop buffer, added sequentially or at one time, function to terminate enzymatic activity, dissociate integrase/DNA complexes, separate non-integrated DNA strands (denaturation agent), and, optionally, float the SPA beads to the surface of the reaction mixture to be closer in range to the detectors of, for example, a plate-based scintillation counter, to measure the level of integrated viral DNA which is quantified as light emitted (radiolabeled signal) from the SPA beads. The inclusion of an additional component in the stop buffer, such as for example CsCl or functionally equivalent compound, is optionally, and preferably, used with a plate-based scintillation counter, for example, with detectors positioned above the assay wells, such as for example a TopCount® counter (PerkinElmer Life Sciences Inc. (Boston, Mass.)). CsCl would not be employed when PMT readings are taken from the bottom of the plate, such as for example when a MicroBeta® counter (PerkinElmer Life Sciences Inc. (Boston, Mass.)) is used.

The specificity of the reaction can be determined from the ratio of the signal generated from the target DNA reaction with the viral DNA/integrase compared to the signal generated from the di-deoxy viral DNA/integrase. High concentrations (e.g., ≧50 nM) of target DNA may increase the d/dd DNA ratio along with an increased concentration of integrase in the integrase/viral DNA sample.

The results can be used to evaluate the integrase modulatory, such as for example inhibitory, activity of test compounds. For example, the skilled artisan may employ a high-throughput screening method to test combinatorial compound libraries or synthetic compounds. The percent inhibition of the compound may be calculated using an equation such as for example (1-((CPM sample−CPM min)/(CPM max−CPM min)))*100. The min value is the assay signal in the presence of a known modulator, such as for example an inhibitor, at a concentration about 100-fold higher than the $IC_{50}$ for that compound. The min signal approximates the true background for the assay. The max value is the assay signal obtained for the integrase-mediated activity in the absence of compound. In addition, the $IC_{50}$ values of synthetic and purified combinatorial compounds may be determined whereby compounds are prepared at about 10 or 100-fold higher concentrations than desired for testing in assays, followed by dilution of the compounds to generate an 8-point titration curve with ½-log dilution intervals, for example. The compound sample is then transferred to an assay well, for example. Further dilutions, such as for example, a 10-fold dilution, are optional. The percentage inhibition for an inhibitory compound, for example, may then be determined as above with values applied to a nonlinear regression, sigmoidal dose response equation (variable slope) using GraphPad Prism curve fitting software (GraphPad Software, Inc., San Diego, Calif.) or functionally equivalent software.

The stINTSPA assay conditions are preferably optimized for ratios of integrase, viral DNA and target DNA to generate a large and specific assay signal. A specific assay signal is defined as a signal distinguishing true strand-transfer catalytic events from complex formation of integrase and DNA that does not yield product. In other integrase assays, a large non-specific component (background) often contributes to the total assay signal unless the buffer conditions are rigorously optimized and counter-tested using a modified viral DNA oligonucleotide. The non-specific background is due to formation of integrase/viral DNA/target DNA complexes that are highly stable independent of a productive strand-transfer mechanism.

The preferred stINTSPA distinguishes complex formation from productive strand-transfer reactions by using a modified viral DNA oligonucleotide containing a di-deoxy nucleoside at the 3' end as a control. This modified control DNA can be incorporated into integrase/viral DNA/target DNA complexes, but cannot serve as a substrate for strand-transfer. Thus, a distinct window between productive and non-productive strand-transfer reactions can be observed. Further, reactions with di-deoxy viral DNA beads give an assay signal closely matched to the true background of the assay using the preferred optimization conditions of the assay. The true background of the assay is defined as a reaction with all assay components (viral DNA and [$^3$H]-target DNA) in the absence of integrase.

Assay buffers used in the integrase assay generally contain at least one reducing agent, such as for example 2-mercaptoethanol or DTT, wherein DTT as a fresh powder is preferred; at least one divalent cation, such as for example $Mg^{++}$, $Mn^{++}$, or $Zn^{++}$, preferably, $Mg^{++}$; at least one emulsifier/dispersing agent, such as for example octoxynol (also known as IGEPAL-CA or NP-40) or CHAPS; NaCl or functionally equivalent compound; DMSO or functionally equivalent compound; and at least one buffer, such as for example MOPS. Key buffer characteristics are the absence of PEG; inclusion of a high concentration of a detergent, such as for example about 1 to about 5 mM CHAPS and/or about 0.02 to about 0.15% IGEPAL-CA or functionally equivalent compound(s) at least capable of reducing non-specific sticking to the SPA beads and assay wells and, possibly, enhancing the specificity index; inclusion of a high concentration of DMSO (about 1 to about 12%); and inclusion of modest levels of NaCl ($\leq 50$ mM) and $MgCl_2$ (about 3 to about 10 mM) or functionally equivalent compounds capable of reducing the dd-DNA background. The assay buffers may optionally contain a preservative, such as for example $NaN_3$, to reduce fungal and bacterial contaminants during storage.

The stop buffer preferably contains EDTA or functionally equivalent compound capable of terminating enzymatic activity, a denaturation agent comprising, for example, NaOH or guanidine hydrochloride, and, optionally, CsCl or functionally equivalent compound capable of assisting in floating the SPA beads to the top of the assay container for scintillation detection at the top of the reservoir and, possibly, minimizing compound interference. An example of an integrase strand-transfer SPA is set forth in Example 13.

Alternatively, the level of activity of the modulatory compounds may be determined in an antiviral assay, such as for example an assay that quantitatively measures the production of viral antigens (e.g., HIV-1 p24) or the activities of viral enzymes (e.g., HIV-1 reverse transcriptase) as indicators of virus replication, or that measures viral replication by monitoring the expression of an exogenous reporter gene introduced into the viral genome (HIV-1 reporter virus assays) (Chen, B. K. et al., *J. Virol.* 68(2): 654–660 (1994); Terwilliger, E. F. et al., *PNAS* 86:3857–3861 (1989)). A preferred method of measuring antiviral activity of a potential modulator compound employs an HIV-1 cell protection assay, wherein virus replication is measured indirectly by monitoring viral induced host-cell cytopathic effects using, for example, dye reduction methods as set forth in Example 14.

In one embodiment, the compounds of the present invention include those having an $EC_{50}$ value against HIV integrase of at least $10^{-5}$ M (or at least 10 µM) when measured with an HIV cell protection assay. In another embodiment are compounds of the present invention with an $EC_{50}$ value against HIV integrase of at least 1 µM when measured with an HIV cell protection assay. In yet another embodiment, the compounds of the present invention have an $EC_{50}$ against HIV integrase of at least 0.1 µM when measured with an HIV cell protection assay.

The inventive agents may be prepared using the reaction routes and synthesis schemes as described below, employing the techniques available in the art using starting materials that are readily available. The preparation of preferred compounds of the present invention is described in detail in the following examples, but the artisan will recognize that the chemical reactions described may be readily adapted to prepare a number of other HIV Integrase agents of the invention. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the invention.

Reagents useful for synthesizing compounds may be obtained or prepared according to techniques known in the art. For example, the preparation of free amines from common salt forms and stock reagent solutions can be useful for small-scale reactions. See also Abdel-Magid et al., "Reductive Amination of Aldehydes and Ketones with Sodium Triacetoxyborohydride," *J. Org. Chem.* 61: 3849 (1996).

Methanolic solutions of the free bases can be prepared from hydrochloride, dihydrochloride, hydrobromide, or other salts when the free base is soluble in methanol. In this procedure, once the sodium methoxide is added, care should be taken to prevent exposure to air, since amine free bases, particularly primary amines, absorb carbon dioxide from the air to form salts. A 10-mL quantity of a 0.1M solution of a free base in methanol may be prepared as follows. Weigh 1.0 mmol of a monohydrochloride salt into a tared Erlenmeyer flask containing a stirring bar, and add 7 mL of methanol. To the stirred slurry, add 229 mL (1.0 mmol, 1 equiv.) of sodium methoxide in methanol (25 wt %, 4.37 M), stopper the flask, and stir the mixture vigorously for 2 hours. The slurry will sometimes change in appearance as a finer, milky precipitate of sodium chloride is formed. Filter the slurry through a 15-mL medium fritted glass funnel, wash the filter case with 1–2 mL methanol, transfer the filtrate to a 20-mL vial, and dilute to 10 mL with methanol. The theoretical yield of sodium chloride is nearly 59 mg, but the recovery is usually not quantitative, owing to a slight solubility in methanol. For a dihydrochloride salt, a second equivalent of sodium methoxide is required (458 mL).

A 0.5 M solution of sodium borohydride in ethanol may be prepared as follows. Sodium borohydride (520 mg, 13.8 mmol) is stirred in pure (non-denatured) anhydrous ethanol (25 mL) for ~2–3 minutes. The suspension is filtered through a medium fritted glass funnel to remove a small amount of undissolved solid (typically about 5% of the total mass of borohydride, or 25 mg). The filtrate should appear as a colorless solution that evolves only a little hydrogen. This solution should be used immediately, as it decomposes significantly over a period of a few hours, resulting in the formation of a gelatinous precipitate. Sodium borohydride is hygroscopic, so avoid exposure to air by making the solution at once after weighing the solid. Sodium borohydride has a solubility of about 4% in ethanol at room temperature. This corresponds to a little over 0.8 M. However, sometimes a small percentage of the solid remains undissolved regardless of the concentration being prepared, even after stirring for $\geq 5$ minutes.

The following abbreviations employed throughout the application have the following meaning unless otherwise indicated:

NaH: sodium hydride;
THF: tetrahydrofuran;
DMF: N,N-dimethylformamide;
TLC: thin-layer-chromatography;
HATU: O-(7-azabenzotriazole-1-yl)-N,N,N',N'-tetramethyl uronium hexafluorophosphate;
EDC: N-(3-dimethylaminopropyl)-N'-ethylcarbodiimide;
DMSO: dimethyl sulfoxide;
DDQ: 2,3-dichloro-5,6-dicyano-1,4-benzoquinone;
MS: molecular sieve(s);
$NaBH_3CN$: sodium cyanoborohydride;
$TiCl_4$: titanium (IV) tetrachloride;
AcOH: acetic acid;

TFA: trifluoro acetic acid;
PPTS: pyridinium p-toluenesulfonate; and
HOBt: 1-hydroxybenzotriazole Additional abbreviations employed throughout the application are either known to those skilled in the art or are explained in the Examples below.

EXAMPLES

The present invention will be further illustrated in the following, non-limiting examples. In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal® bottles and used as received. All solvents were purified using methods standard in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60° F. 254 plates (Analtech (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous $Na_2SO_4$ prior to filtration, and evaporation of the solvents was under reduced pressure on a rotary evaporator and noted as solvents removed in vacuo. Flash column chromatography [Still et al., *A.J. Org. Chem.* 43:2923 (1978)] was conducted using Baker-grade flash silica gel (47–61 mm) and a silica gel: crude material ratio of about 20:1 to 50:1, unless otherwise stated. Hydrogenolysis was done at the pressure indicated or at ambient pressure.

$^1$H-NMR spectra were recorded on a Bruker instrument operating at 300 MHz, 500 MHz, and $^{13}$C-NMR spectra was recorded operating at 75 MHz. NMR spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as $CDCl_3$ solutions, and when reported are in wave numbers ($cm^{-1}$). The mass spectra were obtained using LC/MS or APCI. All melting points are uncorrected.

All final products had greater than 85% purity (by HPLC at wavelengths of 220 nm and 254 nm).

General Procedures

Scheme 1 represents a method for preparing compounds 1-4 of the present invention directly from ester 1-2 (where R is typically a methyl or ethyl and $R_1$–$R_9$ are as defined above) and a substituted or unsubstituted hydroxyl amine, in the absence or presence of a base such as sodium hydroxide in methanol or ethanol (C. R. Hauser, et al., *Org. Synth. Coll.*, Vol. 2, p. 67, John Wiley, New York (1943)). The ester 1-2 can be made by alkylation of compound 1-1 with $R_7X$ in the presence of NaH in DMF or DMSO (M. K. Eberle, *J. Org. Chem.*, 41, 633 (1976); R. J. Sundberg, et al., *J. Org. Chem.*, 38, 3324). Alternatively, the ester 1-2 can be saponified to the free acid 1-3, which can then be coupled with a substituted or unsubstituted hydroxyl amine using a coupling reagent, such as O-(7-azabenzotriazole-1-yl)-N,N,N', N'-tetramethyl uronium hexafluorophosphate (HATU) or N-(3-dimethylaminopropyl)-N-ethylcarbodiimide (EDC), or many others that are familiar to those skilled in the art, to give the compounds 1-4 of the present invention. Suitable methods are described, for example, in Jerry March, *Advanced Organic Chemistry*, 5th edition, pp. 508–511, John Whiley & Sons (2001). Use of the conditions as set forth in the Examples below allows for the parallel preparation or combinatorial syntheses of hydroxamates 1-4.

Scheme 1

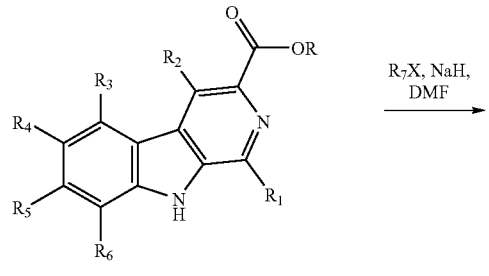

1–1

R$_7$X, NaH,
DMF

-continued
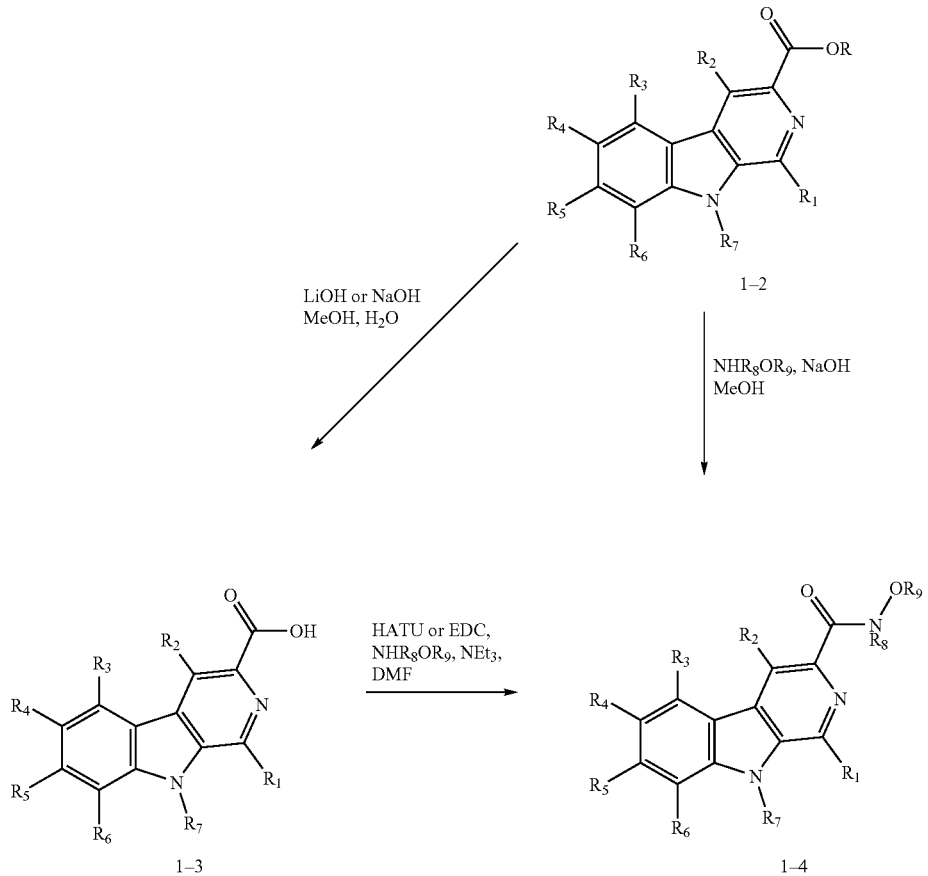
Preparation of Intermediates and Starting Materials
Scheme 2
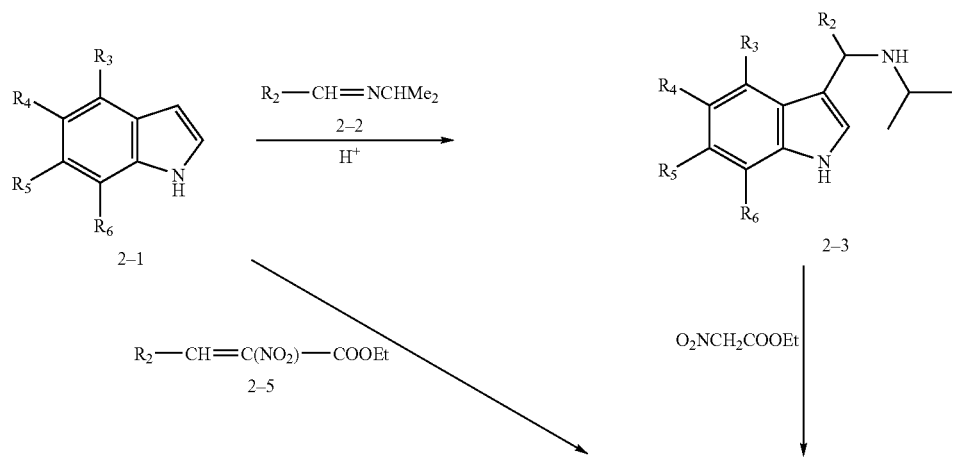

-continued

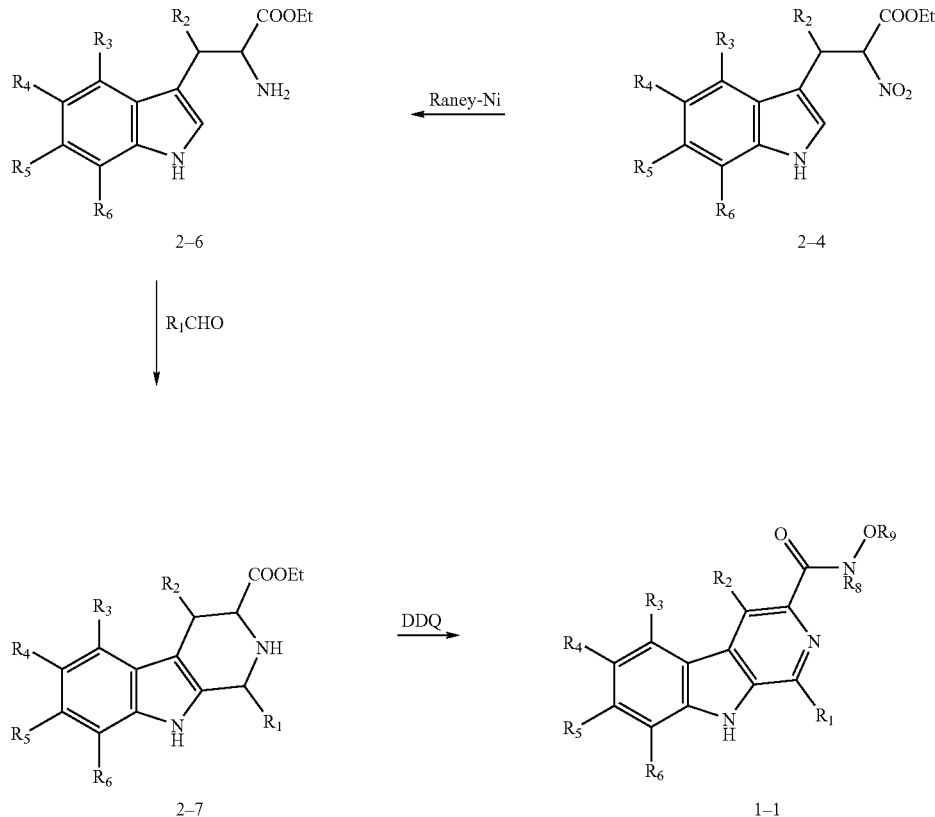

Scheme 2 represents a convenient method for preparation of substituted β-carboline compounds 1-1 (where R=ethyl and $R_2$–$R_6$ are as defined above)(G. Neef, et al., *Heterocycles*, 20, 1295 (1983)). The synthesis employs standard methods of indole chemistry: aldimines 2-2 can be prepared by Campbell's procedure (K. N. Campbell, et al., *J. Am. Chem. Soc.*, 66, 82 (1944)) and reacted with indoles in analogy to Snyder's reaction mode (H. R. Snyder, et al., *J. Am. Chem. Soc.*, 79, 2217 (1957)) to give compounds 2-3. Condensation of compounds 2-3 with ethyl nitro acetate can be performed as described by Lyttle and Erofeev (D. A. Lyttle, et al., *J. Am. Chem. Soc.*, 69, 2118 (1947); Y. V. Erofeev, et al., *Khim. Get. Soed.*, 780 (1978)) to yield nitro compounds 2-4. Compounds 2-4 can also be conveniently obtained by Michael type addition of indoles to the nitro ester 2-5 ($R_2$—CH=C($NO_2$)—COOEt) prepared by condensation of aldehydes ($R_2$CHO) with ethyl nitro acetate ($O_2NCH_2COOEt$). Hydrogenation of compounds 2-4 in the presence of Raney-Ni can give tryptophan derivatives 2-6, as mixtures of isomers. Pictet-Spengler reaction using Sandrin's modification (J. Sandrin et al., *Heterocycles*, 4, 1101 (1976)) can produce tetrahydro-β-carbolines 2-7, which without further purification, can be subjected to oxidation by DDQ (2,3-dichloro-5,6-dicyano-1,4-benzoquinone), sulfur or palladium to afford the desired ester compounds 1-1.

Scheme 3

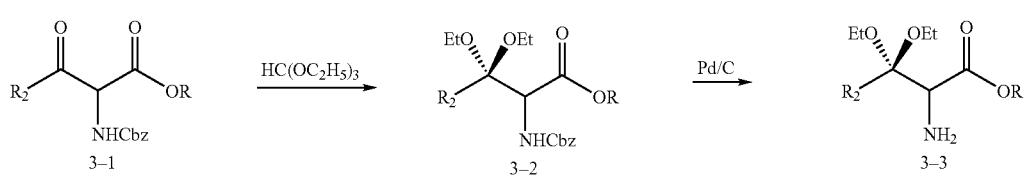

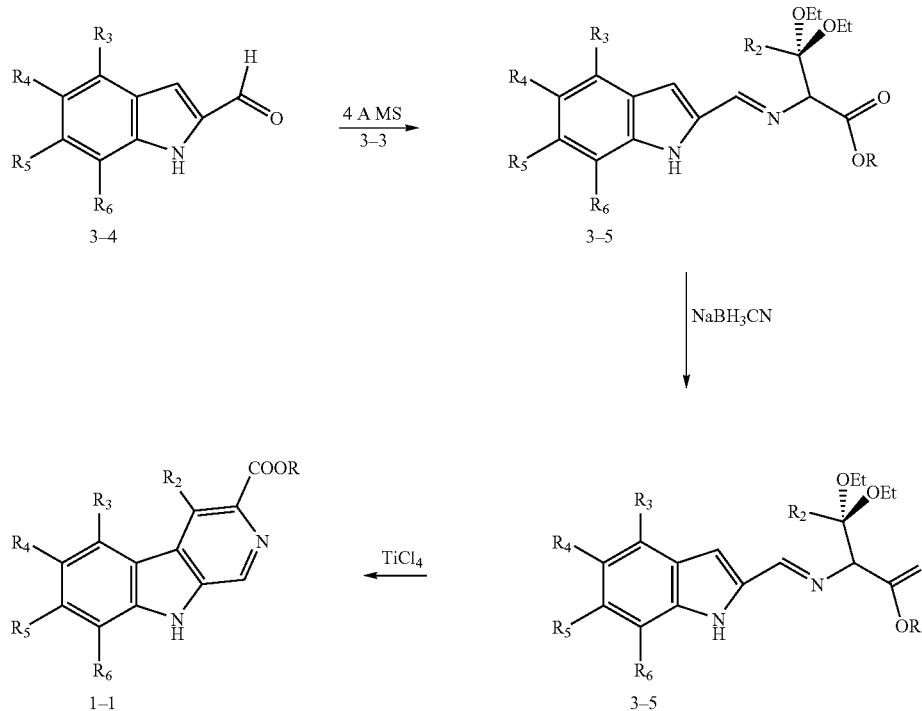

Scheme 3 describes another efficient route to obtain β-carboline esters 1-1 (where R=ethyl or methyl; $R_1$=H; and $R_2$–$R_6$ are as defined above) (M. Dekhane, et al., *Tetrahedron*, 50, 6299 (1994)). Condensation of aldehydes 3-4 and amino ketal 3-3 (prepared by the method of Belleau, T. W. Doyle et al., *Can. J. Chem.*, 55, 468 (1977)) in the presence of 4 Å molecular sieves (MS) can yield imines 3-5, which can be reduced to amines 3-6 with sodium cyanoborohydride ($NaBH_3CN$) in ethanol. On treatment of the amines 3-6 with titanium (IV) tetrachloride ($TiCl_4$) the desired β-carboline esters 1-1 can be obtained.

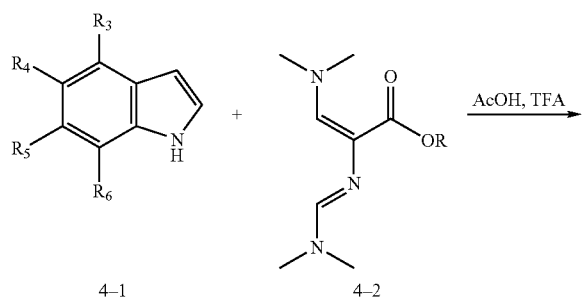

Scheme 4

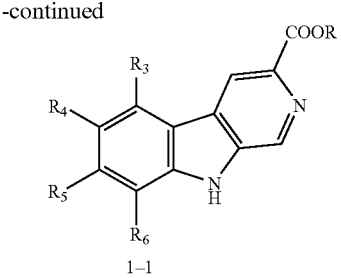

β-Carboline esters 1-1 (where R=methyl or ethyl; $R_1$, $R_2$=H; and $R_3$–$R_6$ are as defined above) can also be prepared by the one pot procedure outlined in Scheme 4. Indole derivatives 4-1 can react with 2-azabutadiene derivatives 4-2 (where R=methyl or ethyl) (W. Kantlehner, et al., *Liebigs Ann. Chem.*, 344 (1980)) in the presence of acetic acid (AcOH) and trifluoro acetic acid (TFA) following the procedures described in H. Biere at al., *Liebigs Ann. Chem.*, 1749 (1986) to form substituted β-carboline esters 1-1 directly.

Scheme 5

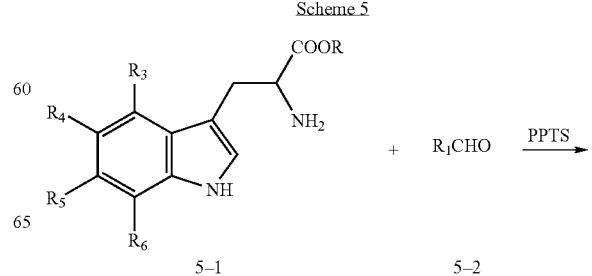

-continued

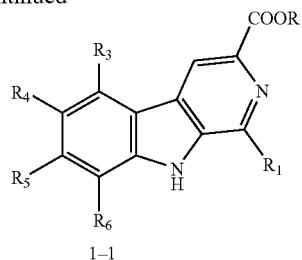

1-1

Scheme 5 represents another method for obtaining substituted β-carboline esters 1-1 (R=methyl or ethyl; $R_2$=H; and $R_1$ and $R_3$–$R_6$ are as defined above). Refluxing of tryptophan derivatives 5-1 with aryl aldehyde 5-2 ($R_1$=aryl) in the presence of pyridinium p-toluenesulfonate (PPTS) in toluene can afford the desired β-carboline esters 1-1 in one step (C. Barbier et al., *Heterocycles*, 1, 37 (2000)).

Other compounds of the Formula I may be prepared in manners analogous to the general procedures described above or the detailed procedures described in the following examples:

Example 1

9-(4-Fluorobenzyl)-N-hydroxy-9H-β-carboline-3-carboxamide

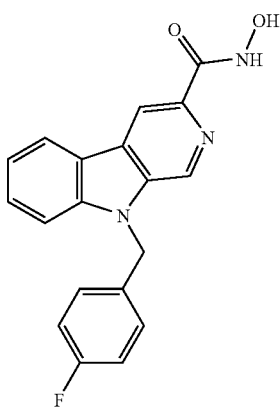

To a stirred solution of ethyl 9H-β-carboline-3-carboxylate (368 mg, 1.53 mmol) in DMF (4 mL) under a nitrogen atmosphere was added NaH (61.2 mg, 60% in mineral oil, 1.53 mmol) portionwise, followed by 4-fluorobenzyl bromide (0.19 mL, 1.53 mmol). Stirring was continued for 24 hours at ambient temperature, water (10 mL) was then added to the mixture. The precipitate was filtered, washed with water and dried to give a solid that was dissolved in methanol (20 mL). To the resulting solution, $H_2NOH$ (20 mL, 50 wt. % solution in $H_2O$, 0.30 mol) was added. The suspension was stirred for 5 days at ambient temperature. The mixture was then filtered, and the solid was boiled in methanol (40 mL). After filtration, the title product (0.20 g, 39%) was obtained. $^1$H NMR (300 MHz, DMSO-$d_6$): δ 11.28 (1H, s), 9.02–9.08 (2H, m), 8.85 (1H, s), 8.48 (1H, d, J=9.0 Hz), 7.10–7.84 (7H, m), 5.85 (2H, s). HRMS (M+H)$^+$ found: 336.1157. Calcd for $C_{19}H_{15}N_3O_2F$: 336.1148.

Example 2

9-[(5-Chlorothien-2-yl)methyl]-N-hydroxy-9H-β-carboline-3-carboxamide

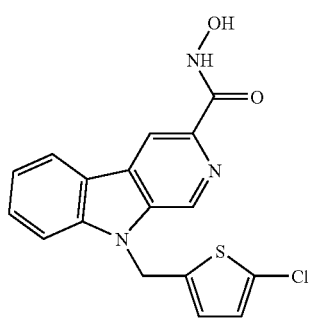

To a stirred solution of ethyl 9H-β-carboline-3-carboxylate (300 mg, 1.25 mmol) in DMF (3 mL) under a nitrogen atmosphere was added NaH (50.0 mg, 60% in mineral oil, 1.25 mmol) portionwise, followed by 2-chloro-5-(chloromethyl)-thiophene (151 μL, 1.25 mmol). The stirring was continued for 21 hours at ambient temperature, water (50 mL) was then added to the mixture. The precipitate was filtered, washed with water and dried to give a solid that was dissolved in methanol (25 mL). To the resulting solution, $H_2NOH$ (25 mL, 50 wt. % solution in $H_2O$, 0.38 mol) was added. The suspension was stirred for 4 days at ambient temperature. The mixture was then filtered, and the solid was boiled in methanol (25 mL). After filtration, the desired product (0.26 g, 58%) was obtained. $^1$H NMR (400 MHz, DMSO-$d_6$): 11.28 (1H, s), 9.15 (1H, s), 9.01 (1H, s), 8.81 (1H, s), 8.44 (1H, d, J=8 Hz), 6.94–7.92 (5H, m) 5.99 (2H, s). HRMS (M+H)$^+$ found: 358.0417. Calcd for $C_{17}H_{13}N_3O_2SCl$: 358.0417.

Example 3

9-(3-Chloro-2-fluorobenzyl)-N-hydroxy-9H-β-carboline-3-carboxamide

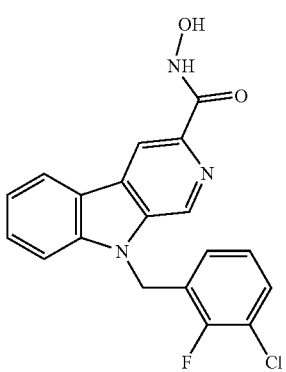

To a stirred solution of ethyl 9H-β-carboline-3-carboxylate (400 mg, 1.66 mmol) in DMF (5 mL) under nitrogen atmosphere was added NaH (66.4 mg, 60% in mineral oil, 1.66 mmol) portionwise, followed by 3-chloro-2-fluorobenzyl bromide (371 mg, 1.66 mmol). Stirring was continued for 25 hours at ambient temperature, water (30 mL) was then added to the mixture. The precipitate was filtered, washed with water and dried to give a solid that was dissolved in methanol (25 mL). To the resulting solution, H$_2$NOH (25 mL, 50 wt. % solution in H$_2$O, 0.38 mol) was added. The suspension was stirred for 4 days at ambient temperature. The mixture was then filtered, and the solid was boiled in methanol (20 mL). After filtration, the title product (0.19 g, 31%) was obtained. $^1$H NMR (400 MHz, DMSO-d$_6$): δ 11.33 (1H, s), 9.08 (1H, s), 9.04 (1H, s), 8.89 (1H, s), 8.51 (1H, d, J=8 Hz), 6.95–7.81 (6H, m), 6.00 (2H, s). HRMS (M+H)$^+$ found: 370.0764. Calcd for C$_{19}$H$_{14}$N$_3$O$_2$FCl: 370.0759.

Example 4

9-Benzyl-N-hydroxy-9H-β-carboline-3-carboxamide

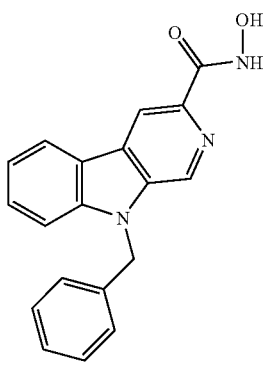

To a stirred solution of ethyl 9H-β-carboline-3-carboxylate (290 mg, 1.21 mmol) in DMF (4 mL) under a nitrogen atmosphere was added NaH (53 mg, 60% in mineral oil, 1.33 mmol) portionwise, followed by benzyl bromide (173 μL, 1.45 mmol). Stirring was continued for 21 hours at ambient temperature, water (50 mL) was then added to the mixture. The precipitate was filtered, washed with water and dried to give a solid that was dissolved in methanol (25 mL). To the resulting solution, H$_2$NOH (25 mL, 50 wt. % solution in H$_2$O, 0.38 mol) was added. The suspension was stirred for 3 days at ambient temperature. The mixture was then filtered, and the solid was boiled in methanol (25 mL). After filtration, the title product (0.15 g, 39%) was obtained. $^1$H NMR (400 MHz, DMSO-d$_6$): δ 11.32 (1H, s), 9.10 (1H, s), 9.05 (1H, s), 8.89 (1H, s), 8.52 (1H, d, J=8 Hz), 7.26–7.87 (8H, m), 5.90 (2H, s). HRMS (M+H)$^+$ found: 318.1249. Calcd for C$_{19}$H$_{16}$N$_3$O$_2$: 318.1243.

Example 5

9-(4-Methylbenzyl)-N-Hydroxy-9H-β-carboline-3-carboxamide

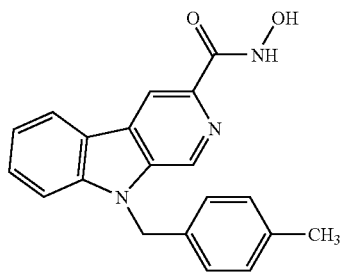

To a stirred solution of ethyl 9H-β-carboline-3-carboxylate (400 mg, 1.67 mmol) in DMF (5 mL) under a nitrogen atmosphere was added NaH (73 mg, 60% in mineral oil, 1.76 mmol) portionwise, followed by 4-methylbenzyl bromide (308 mg, 1.67 mmol). Stirring was continued for 48 hours at ambient temperature, water (50 mL) was then added to the mixture. The precipitate was filtered, washed with water and dried to give a solid that was dissolved in methanol (35 mL). To the resulting solution, NaOH (2N, 1 mL) and H$_2$NOH (35 mL, 50 wt. % solution in H$_2$O, 0.53 mol) were added. The suspension was stirred for 7 days at ambient temperature. The mixture was then filtered and dried to the title product (0.20 g, 36%). $^1$H NMR (400 MHz, DMSO-d$_6$): δ 11.25 (1H, s), 8.95–9.03 (2H, m), 8.83 (1H, s), 8.45 (1H, d, J=8 Hz), 7.05–7.81 (7H, m), 5.78 (2H, s), 2.21 (3H, s). HRMS (M+H)$^+$ found: 332.1400. Calcd for C$_{20}$H$_{18}$N$_3$O$_2$: 332.1399.

Example 6

9-(2,4-Difluorobenzyl)-N-hydroxy-9H-β-carboline-3-carboxamide

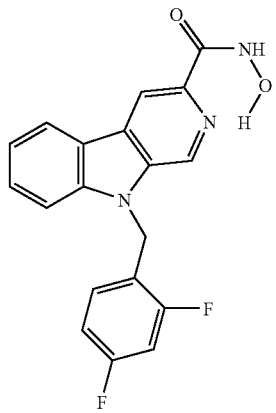

To a stirred solution of ethyl 9H-β-carboline-3-carboxylate (370 mg, 1.54 mmol) in DMF (5 mL) under a nitrogen atmosphere was added NaH (61.6 mg, 60% in mineral oil, 1.54 mmol) portionwise, followed by 2,4-difluorobenzyl bromide (198 μL, 1.54 mmol). Stirring was continued for 48 hours at ambient temperature, water (100 mL) was then added to the mixture. The precipitate was filtered, washed with water and dried to give a solid that was dissolved in methanol (35 mL). To the resulting solution, H$_2$NOH (30 mL, 50 wt. % solution in H$_2$O, 0.45 mol) was added. The suspension was stirred for 4 days at ambient temperature. The mixture was then filtered, and the solid was recrystallized from methanol to give the title product (0.20 g, 37%). $^1$H NMR (400 MHz, DMSO-d$_6$): δ 11.46 (1H, s), 9.15–9.22 (2H, m), 9.02 (1H, s), 8.64 (1H, d, J=8 Hz), 7.15–7.96 (6H, m), 6.06 (2H, s). HRMS (M+H)$^+$ found: 354.1062. Calcd for C$_{19}$H$_{14}$F$_2$N$_3$O$_2$FCl: 354.1054.

Example 7

9-(3-Chloro-2,6-difluorobenzyl)-N-hydroxy-9H-β-carboline-3-carboxamide

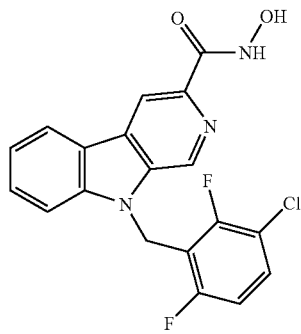

Step (a): Ethyl 9-(3-chloro-2,6-difluorobenzyl)-9H-β-carboline-3-carboxylate

To a stirred solution of ethyl 9H-β-carboline-3-carboxylate (440 mg, 1.83 mmol) in DMF (5 mL) under a nitrogen atmosphere was added NaH (73.3 mg, 60% in mineral oil, 1.83 mmol) portionwise, followed by 3-chloro-2,6-difluorobenzyl bromide (442 mg, 1.83 mmol). Stirring was continued for 22 hours at ambient temperature, water (30 mL) was then added to the mixture. The precipitate was filtered, washed with water and dried to give the title product (0.55 g, 68%). $^1$H NMR (400 MHz, CD$_3$OD): δ 9.04 (1H, s), 8.86 (1H, s), 8.26 (1H, d, J=8 Hz), 6.98–7.69 (5H, m), 5.82 (2H, s), 4.44 (2H, q, J=8 Hz), 1.43 (3H, t, J=8 Hz).

Step (b): 9-(3-Chloro-2,6-difluorobenzyl)-N-hydroxy-9H-β-carboline-3-carboxamide To a stirred solution of ethyl 9-(3-chloro-2,6-difluorobenzyl)-9H-β-carboline-3-carboxylate (260 mg, 0.649 mmol) in methanol (25 mL) under a nitrogen atmosphere was added LiOH (4 mL, 1N in H$_2$O, 4.0 mmol). The stirring was continued for 24 hours at ambient temperature, 20% of citric acid was then added to neutralize the mixture. The solvents were removed under reduced pressure. H$_2$O (20 mL) was finally added to the resulting residue, and the precipitates were collected, washed with water and dried to give the corresponding acid (169 mg, 70%) that was directly used for the next step.

To the stirred solution of the acid (169 mg, 0.45 mmol) in DMF (8 mL) were added 1-[3-(dimethylamino)propyl]-3-ethyl-carbodiimide hydrochloride (EDC, 234 mg, 1.22 mmol) and HOBt (142 mg, 1.05 mmol). The mixture was stirred for 1 h, and then triethylamine (0.62 ml, 4.4 mmol) and hydroxylamine hydrochloride (243 mg, 3.49 mmol) were added. The resulting mixture was stirred for 48 h at ambient temperature, and then water (100 mL) was added. The precipitates were collected, washed with methanol, and dried to give the title compound (130 mg, 74%). $^1$H NMR (400 MHz, DMSO-d$_6$): δ 11.32 (1H, s), 9.01–9.04 (2H, m), 8.83 (1H, s), 8.45 (1H, d, J=8 Hz), 7.22–7.73 (5H, m), 5.95 (2H, s). HRMS (M+H)$^+$ found: 388.0674. Calcd for C$_{19}$H$_{13}$ClF$_2$N$_3$O$_2$: 388.0664.

Example 8

6-Amino-9-(3-chlorobenzyl)-N-hydroxy-9H-β-carboline-3-carboxamide

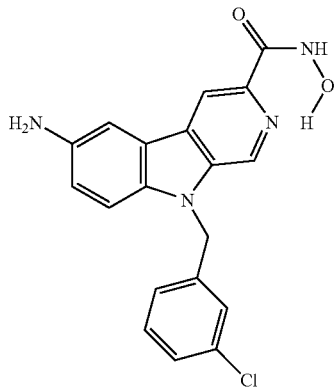

Step (a): Ethyl 9-(3-chlorobenzyl)-6-nitro-9H-β-carboline-3-carboxylate

The title compound was prepared by alkylation of ethyl 6-nitro-9H-β-carboline-3-carboxylate (prepared according to Settimj, et. al., *J. Heterocycl. Chem.*, 25, 1391–1397 (1988)) with 3-chlorobenzyl chloride in a manner similar to step (a) of example 7. LCMS (APCI, M+H$^+$): 410.1/412.1=3/1.

Step (b): Ethyl 6-amino-9-(3-chlorobenzyl)-9H-β-carboline-3-carboxylate

A solution of ethyl 9-(3-chlorobenzyl)-6-nitro-9H-β-carboline-3-carboxylate (2.7 g, 6.59 mmol) and titanium(III) chloride (36 mL, 20% solution, 46.75 mmol) in a mixture of acetic acid (54 mL), THF (180 mL), water (54 mL) and DMF (10 mL) was stirred for 5 hours at ambient temperature. The reaction mixture was quenched with water (200 mL), and extracted with ethyl acetate (100 mL). The pH of the water layer was adjusted to 7 with saturated $Na_2CO_3$ aqueous solution. Then, the resulting precipitate was filtered and dried in vacuo. The product was extracted from the precipitate with $CHCl_3$ in a Soxhlet extractor and purified by chromatography with ethyl acetate to provide the title compound (0.70 g, yield 27.8%). $^1$H NMR (DMSO-$d_6$): δ 9.06 (s, 1H), 8.70 (s, 1H), 7.50 (d, 1H, J=8.0 Hz), 7.45 (s, 1H), 7.27–7.31 (m, 3H), 7.09 (s, 1H), 7.01 (d, 1H, J=8.0 Hz), 5.75 (s, 2H), 5.05 (s, 2H), 4.36 (q, 2H, J=7.0 Hz), 1.35 (t, 3H, J=7.0 Hz). LCMS (APCI, M+H$^+$): 380.1/382.1=3/1.

Step (c): 6-Amino-9-(3-chlorobenzyl)-N-hydroxy-9H-β-carboline-3-carboxamide

To a stirred solution of ethyl 6-amino-9-(3-chlorobenzyl)-9H-β-carboline-3-carboxylate (139 mg, 0.37 mmol) in methanol (15 mL) under a nitrogen atmosphere were added NaOH (2N, 0.7 mL) and $H_2NOH$ (15 mL, 50 wt. % solution in $H_2O$, 0.23 mol). The suspension was stirred for 7 days at ambient temperature and then diluted with $H_2O$ (10 mL). The mixture was filtered, and the solid was boiled in methanol (20 mL). After filtration, the title compound (36 mg, 27%) was obtained. $^1$H NMR (400 MHz, DMSO-$d_6$): δ 11.17 (1H, s), 8.90–8.95 (2H, m), 8.55 (1H, s), 6.96–7.51 (7H, m), 5.72 (2H, s), 5.03 (2H, br, s). HRMS (M+H)$^+$ found: 367.0961. Calcd for $C_{19}H_{16}ClN_4O_2$: 367.0962.

Example 9

9-(3-Chloro-2,6-difluorobenzyl)-N-methoxy-9H-β-carboline-3-carboxamide

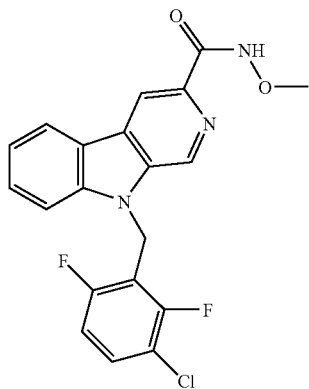

The title compound is prepared by coupling of 9-(3-chloro-2,6-difluorobenzyl)-9H-β-carboline-3-carboxylic acid and O-methyl hydroxylamine hydrochloride under conditions similar to those provided in step (b) of example 7.

Example 10

N-(Benzyloxy)-9-(3-chloro-2,6-difluorobenzyl)-9H-β-carboline-3-carboxamide

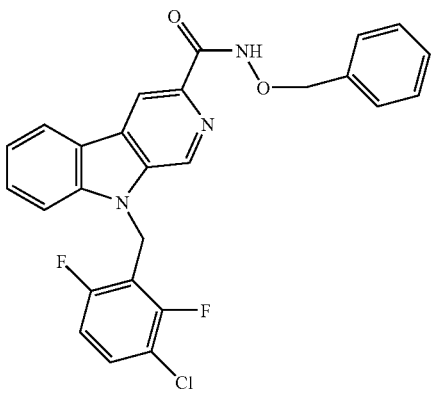

The title compound is prepared by coupling of 9-(3-chloro-2,6-difluorobenzyl)-9H-β-carboline-3-carboxylic acid and O-benzyl hydroxyamine under conditions similar to those provided in step (b) of example 7.

Example 11

9-(3-Chloro-2,6-difluorobenzyl)-N-hydroxy-N-methyl-9H-□-carboline-3-carboxamide

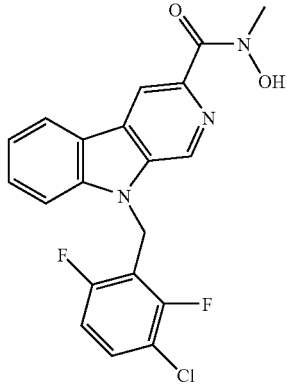

The title compound is prepared by coupling of 9-(3-chloro-2,6-difluorobenzyl)-9H-β-carboline-3-carboxylic acid and N-methyl hydroxylamine hydrochloride under conditions similar to those provided in step (b) of example 7.

Example 12

N-Benzyl-9-(3-chloro-2,6-difluorobenzyl)-N-hydroxy-9H-β-carboline-3-carboxamide

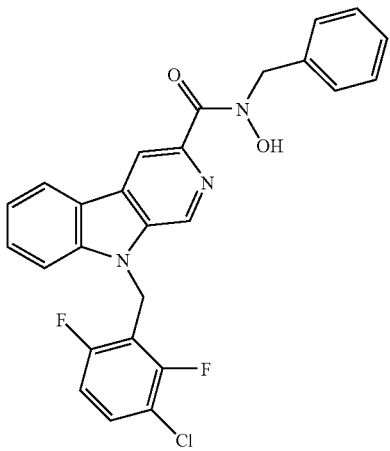

The title compound is prepared by coupling of 9-(3-chloro-2,6-difluorobenzyl)-9H-β-carboline-3-carboxylic acid and N-benzyl hydroxylamine hydrochloride under conditions similar to those provided in step (b) of example 7.

Example 13

9-(4-Fluorobenzyl)-N-hydroxy-N-methyl-9H-β-carboline-3-carboxamide

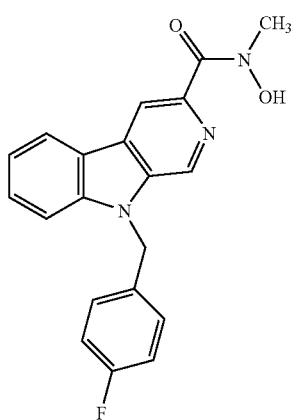

The title compound can be prepared from ethyl 9-(4-fluorobenzyl)-9H-β-carboline-3-carboxylate under the similar conditions as those in steps (a) and (b) of example 7. $^1$H NMR (400 MHz, CD$_3$OD): δ 8.60–8.95 (2H, m), 8.32 (1H, d, J=8 Hz), 7.60–7.75 (2H, m), 6.95–7.45 (5H, m), 5.76 (2H, s), 3.48 (3H, s). HRMS (M+H)$^+$ found: 350.1297. Calcd for $C_{20}H_{17}FN_3O_2$: 350.1305.

Example 14

Integrase Strand-Transfer Scintillation Proximity Assay

Oligonucleotides: Oligonucleotide #1-5'-(biotin) CCCCTTTTAGTCAGTGTGGAAAATCTCTAGCA-3' (SEQ ID NO: 1) and oligonucleotide #2-5'-ACTGCTAGAGATTTTCCACACTGACTAAAAG-3' (SEQ ID NO: 2), were synthesized by TriLink BioTechnologies, Inc. (San Diego, Calif.). The annealed product represents preprocessed viral ds-DNA derived from the LTR U5 sequence of the viral genome. A ds-DNA control to test for non-specific interactions was made using a 3' di-deoxy derivative of oligonucleotide #1 annealed to oligonucleotide #2. The CA overhang at the 5' end of the non-biotinylated strand of the ds-DNA was created artificially by using a complimentary DNA oligonucleotide shortened by 2 base pairs. This configuration eliminates the requisite 3' processing step of the integrase enzyme prior to the strand-transfer mechanism.

Host ds-DNA was prepared as an unlabeled and [$^3$H]-thymidine labeled product from annealed oligonucleotide #3-5-AAAAAATGACCAAGGGCTAATTCACT-3' (SEQ ID NO: 3), and oligonucleotide #4-5'-AAAAAAAGT-GAATTAGCCCTTGGTCA-3' (SEQ ID NO: 4), both synthesized by TriLink BioTechnologies, Inc. (San Diego, Calif.). The annealed product had overhanging 3' ends of poly(dA). Host DNA was custom radiolabeled by PerkinElmer Life Sciences Inc. (Boston, Mass.) using an enzymatic method with a 12/1 ratio of [methyl-$^3$H]dTTP/cold ds-DNA to yield 5'-blunt end ds-DNA with a specific activity of >900 Ci/mmol. The radiolabeled product was purified using a NENSORB cartridge and stored in stabilized aqueous solution (PerkinElmer). The final radiolabeled product had six [$^3$H]-thymidine nucleotides at both 5' ends of the host ds-DNA.

Reagents: Streptavidin-coated polyvinyltoluene (PVT) SPA beads were purchased from Amersham Pharmacia (Piscataway, N.J.). Cesium chloride was purchased from Shelton Scientific, Inc. (Shelton, Conn.). White polystyrene, flat bottom, non-binding surface 384-well plates were purchased from Corning. All other buffer components were purchased from Sigma (St. Louis, Mo.) unless otherwise indicated.

Enzyme Construction: Full-length HIV-1 integrase (SF1) sequence (amino acids 1–288) (SEQ ID NO: 5) was constructed in a pET 15b vector (Novagen, Madison, Wis.) with mutations outlined by Chen et al. (Chen, C-H. J. et al., *PNAS* 97: 8233–8238 (2000)) that facilitate solubility of the enzyme and decrease oxidation. The vector contained a T7 promoter, a 6-histidine tag at the amino terminus, and a thrombin cleavage site. Mutations C56S, W131D, F139D, F185K, and C280S were introduced using a QuickChange kit (Stratagene, San Diego, Calif.). The construct was confirmed through DNA sequencing.

Enzyme Purification: The penta-mutant was expressed in *E. coli* BL21 (DE3) cells and induced with 1 mM isopropyl-1 thio-β-D-galactopyranoside (IPTG) when cells reached an optical density between 0.8–1.0 at 600 nm. Cells were lysed in 20 mM HEPES (pH 7.5), 1.5 M NaCl, 5 mM imidazole, and 2 mM 2-mercaptoethanol. The enzyme was purified following standard methods for histidine tagged proteins (Jenkins, T. M. et al., *Journal of Biological Chemistry* 271: 7712–7718 (1996)). Specifically, cell lysate was passed over a Ni-Nta column (Qiagen, Chatsworth, Calif.) with the 6-His tagged integrase protein eluted by adding 250 mM imidazole. A G-25 Sepharose® column (Amersham Pharmacia, Piscataway, N.J.) was used to exchange the buffer prior to thrombin cleavage of the integrase protein and subsequent removal of thrombin using a benzamidine-Sepharose® 6B column. The cleaved 6-His tag was separated from the integrase using a second Ni-Nta column. The integrase was further purified with a heparin-Sepharose® column and a gradient of NaCl (0.4 to 1 M) in 20 mM HEPES (pH 7.5), 400 mM NaCl, and 1 mM DTT buffer. The purified protein was dialyzed against 20 mM HEPES (pH 7.5), 800 mM NaCl, and 1 mM DTT and concentrated by stirred cell ultrafiltration (Millipore, Bedford, Mass.) or Ultra-free spin concentrators (Millipore, Bedford, Mass.) when required.

Viral DNA Bead Preparation: Streptavidin-coated SPA beads were suspended to 20 mg/ml in 25 mM 3-morpholinopropanesulfonic acid (MOPS) (pH 7.2) and 0.1% $NaN_3$. Biotinylated viral DNA was bound to the hydrated SPA beads in a batch process by combining 25 pmoles of ds-DNA to 1 mg of suspended SPA beads (10 µl of 50 µM viral DNA to 1 ml of 20 mg/ml SPA beads). The mixture was incubated at 22° C. for 20 min. with occasional mixing followed by centrifugation at about 2500 rpm for about 10 min. However, the centrifugation speed and time may vary depending upon the particular centrifuge and conditions. The supernatant was removed and the beads suspended to 20 mg/ml in 25 mM MOPS (pH 7.2) and 0.1% $NaN_3$. The viral DNA beads were stable for more than 2 weeks when stored at 4° C. Di-deoxy viral DNA was prepared in an identical manner to yield control di-deoxy viral DNA beads.

Preparation of Integrase-DNA Complex: Assay buffer was made as a 10× stock of 250 mM MOPS (pH 7.2), 250 mM NaCl, 50 mM 3-[(3-cholamidopropyl)dimethylammonio]-1-propanesulfonate (CHAPS), 0.5% (octylphenoxy) polyethoxyethanol (NP40) (IGEPAL-CA) and 0.05% $NaN_3$. Viral DNA beads were diluted to 2.67 mg/ml in 1× assay buffer plus 3 mM $MgCl_2$, 1% DMSO, and 10 mM fresh DTT. Integrase (IN) was pre-complexed to viral DNA beads in a batch process (IN/viral DNA/bead complex) by combining diluted viral DNA beads with integrase at a concentration of 385 nM followed by a minimum incubation time of 15 min. at 22° C. The sample was kept at 22° C. until transferred to the assay wells. Long-term storage at 4° C. was possible, but not routinely applied.

Preparation of Host DNA: Host DNA was prepared to 200 nM as a mixture of unlabeled and [$^3$H]T-labeled host DNA diluted in 1× assay buffer plus 8.5 mM $MgCl_2$ and 15 mM DTT. Typical concentrations were about 10 nM to about 12 nM [$^3$H]T-labeled host DNA and about 188 nM to about 190 nM unlabeled host DNA. The ratio was adjusted relative to enzyme activity and specific activity of the [$^3$H]T-labeled host DNA to generate a SPA assay signal of 2000–3000 CPM in the absence of modulators such as inhibitors.

Strand-transfer Scintillation Proximity Assay: The strand-transfer reaction was carried out in 384-well microtiter plates, though an identical protocol can be used for a 96-well plate format with a final enzymatic reaction volume of 50 µl. Five microliters of compounds or test reagents diluted in 10% DMSO were added to the assay wells followed by the addition of 32.5 µl of the IN/viral-DNA/bead complex. The strand-transfer reaction was initiated by adding 12.5 µl of host DNA with vigorous vortexing of the plates and transferring them to a humidified 37° C. incubator. An incubation time of 50 min. was shown to be within the linear range of the enzymatic reaction in a 384-well plate. Reaction kinetics are faster in a 96-well format. An incubation time of 20 or 50 minutes was used as the time point to evaluate compound inhibitors for assays run in the 96- or 384-well plate format, respectively. The final concentrations of integrase and host DNA in the assay wells were 246 nM and 50 nM, respectively.

The integrase strand-transfer reaction was terminated by adding 35 µl of stop buffer (150 mM EDTA, 90 mM NaOH, and 6 M CsCl) to the wells. Components of the stop buffer function to terminate enzymatic activity (EDTA), dissociate integrase/DNA complexes in addition to separating non-integrated DNA strands (NaOH), and float the SPA beads to the surface of the wells to be in closer range to the PMT detectors of the TopCount® plate-based scintillation counter (PerkinElmer Life Sciences Inc. (Boston, Mass.)). After the addition of stop buffer, the plates were vigorously vortexed, sealed with transparent tape, and allowed to incubate a minimum of 60 min. at 22° C. The assay signal was measured using a TopCount® plate-based scintillation counter with settings optimal for [3H]-PVT SPA beads. The TopCount® program incorporated a quench standardization curve to normalize data for color absorption of the compounds (color quench correction program (QstINT file). Data values for quench-corrected counts per minute (QCPM) were used to quantify integrase activity. Counting time was 30 sec./well for plates processed in HTS mode, and up to 2 min./well for plates containing purified compound.

The di-deoxy viral DNA beads were used to optimize the integrase strand-transfer reaction. The di-deoxy termination of the viral ds-DNA sequence prevented productive integration of viral DNA into the host DNA by integrase. Thus, the assay signal in the presence of di-deoxy viral DNA was a measure of non-specific interactions. Assay parameters were optimized to where reactions with di-deoxy viral DNA beads gave an assay signal closely matched to the true background of the assay. The true background of the assay was defined as a reaction with all assay components (viral DNA and [$^3$H]-host DNA) in the absence of integrase.

Determination of Compound Activity: Compounds were evaluated for integrase inhibitory activity using two different methods. A high-throughput screening method was employed to test combinatorial compound libraries or synthetic compounds that were solvated and transferred to microtiter plates. The percent inhibition of the compound was calculated using the equation (1−((QCPM sample−QCPM min)/(QCPM max−QCPM min)))*100. The min value is the assay signal in the presence of a known inhibitor at a concentration 100-fold higher than the $IC_{50}$ for that compound. The min signal approximates the true background for the assay. The max value is the assay signal obtained for the integrase-mediated activity in the absence of compound.

The $IC_{50}$ values of synthetic and purified combinatorial compounds were also determined. Compounds were prepared in 100% DMSO at 100-fold higher concentrations than desired for testing in assays, followed by dilution of the compounds in 100% DMSO to generate an 8-point titration curve with ½-log dilution intervals. The compound sample was further diluted 10-fold with water and transferred to the assay wells. The percentage inhibition for an inhibitory compound was determined as above with values applied to a nonlinear regression, sigmoidal dose response equation (variable slope) using GraphPad Prism curve fitting software (GraphPad Software, Inc., San Diego, Calif.).

| Compound | IC$_{50}$ (µM)* |
|---|---|
| 1 | 0.234 |
| 2 | 0.494 |
| 3 | 0.4 |
| 4 | 0.281 |
| 5 | 9% inhibition at 50 µM |
| 6 | 0.463 |
| 7 | 1.39 |
| 8 | 0.713 |
| 13 | 0.699 |

*The error associated with each of these measurements is not shown

Example 14

HIV-1 Cell Protection Assay

The antiviral activities of potential modulator compounds (test compounds) were determined in HIV-1 cell protection assays using the RF strain of HIV-1, CEM-SS cells, and the XTT dye reduction method (Weislow, O. S. et al., *J. Natl. Cancer Inst.* 81: 577–586 (1989)). Subject cells were infected with HIV-1 RF virus at an moi of 0.025 to 0.819 or mock infected with medium only and added at 2×10$^4$ cells per well into 96 well plates containing half-log dilutions of test compounds. Six days later, 50 µl of XTT (1 mg/ml XTT tetrazolium and 0.02 nM phenazine methosulfate) were added to the wells and the plates were reincubated for four hours. Viability, as determined by the amount of XTT formazan produced, was quantified spectrophotometrically by absorbance at 450 nm.

Data from CPE assays were expressed as the percent of formazan produced in compound-treated cells compared to formazan produced in wells of uninfected, compound-free cells. The fifty percent effective concentration (EC$_{50}$) was calculated as the concentration of compound that affected an increase in the percentage of formazan production in infected, compound-treated cells to 50% of that produced by uninfected, compound-free cells. The 50% cytotoxicity concentration (CC$_{50}$) was calculated as the concentration of compound that decreased the percentage of formazan produced in uninfected, compound-treated cells to 50% of that produced in uninfected, compound-free cells. The therapeutic index was calculated by dividing the cytotoxicity (CC$_{50}$) by the antiviral activity (EC$_{50}$).

It is to be understood that the foregoing description is exemplary and explanatory in nature, and is intended to illustrate the invention and its preferred embodiments. Thus, the scope of the invention should be understood to be defined not by the foregoing description, but by the following claims and their equivalents.

We claim:

1. A compound of formula (Ib),

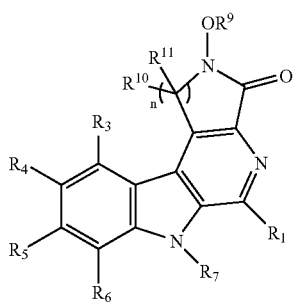

wherein:

$R_1$, $R_3$, $R_4$, $R_5$, and $R_6$ are independently selected from hydrogen, halogen, $C_1$–$C_6$ alkyl, alkoxy $C_1$–$C_6$ alkyl, $C_2$–$C_6$ alkenyl, $C_2$–$C_6$ alkynyl, —$OR_c$, —$NO_2$, and —$N(R_c)_2$;

each $R_c$ is independently selected from hydrogen, $C_1$–$C_6$ alkyl, $C_2$–$C_6$ alkenyl, and $C_2$–$C_6$ alkynyl;

$R_7$ is $C_1$–$C_6$ alkyl, $C_2$–$C_6$ alkenyl, or $C_2$–$C_6$ alkynyl, all of which are optionally substituted by one or more substituents independently selected from halogen, $C_1$–$C_6$ alkyl, $C_2$–$C_6$ alkenyl, $C_2$–$C_6$ alkynyl, aryl, cycloalkyl, heterocycloalkyl, and heteroaryl, wherein said aryl, cycloalkyl, and heterocycloalkyl are optionally substituted with one or more substituents independently selected from halogen, $C_1$–$C_6$ alkyl, $C_2$–$C_6$ alkenyl, and $C_2$–$C_6$ alkynyl;

$R_9$ is independently selected from hydrogen, $C_1$–$C_6$ alkyl, $C_2$–$C_6$ alkenyl, and $C_2$–$C_6$ alkynyl, wherein said alkyl, alkenyl, and alkynyl are optionally substituted with one or more substituents independently selected from halogen, aryl, cycloalkyl, heterocycloalkyl, and heteroaryl group, wherein said aryl, cycloalkyl, and heterocycloalkyl are optionally substituted with one or more substituents independently selected from halogen, $C_1$–$C_6$ alkyl, $C_2$–$C_6$ alkenyl, and $C_2$–$C_6$ alkynyl;

each $R_{10}$ and $R_{11}$ are independently selected from hydrogen, halogen, $C_1$–$C_6$ alkyl, $C_2$–$C_6$ alkenyl, and $C_2$–$C_6$ alkynyl, —$OR_c$, or —$N(R_c)_2$ group, wherein said alkyl, alkenyl, and alkynyl are optionally substituted by one or more substituents selected from halogen, aryl, cycloalkyl, heterocycloalkyl, and heteroaryl group, wherein said aryl, cycloalkyl, heterocycloalkyl, and heteroaryl are optionally substituted with at least one substituent independently selected from halogen, $C_1$–$C_6$ alkyl, $C_2$–$C_6$ alkenyl, and $C_2$–$C_6$ alkynyl; and n is 1, 2 or 3; or a pharmaceutically acceptable salt or solvate thereof.

2. A pharmaceutical composition, comprising a therapeutically effective amount of at least one compound according to claim 1 and a pharmaceutically acceptable carrier, diluent, or vehicle.

* * * * *

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial
<220> FEATURE:
<223> OTHER INFORMATION: Oligonucleotide

<400> SEQUENCE: 1
ccccttttag tcagtgtgga aaatctctag ca                          32

<210> SEQ ID NO 2
<211> LENGTH: 31
<212> TYPE: DNA
<213> ORGANISM: Artificial
<220> FEATURE:
<223> OTHER INFORMATION: Oligonucleotide

<400> SEQUENCE: 2
actgctagag attttccaca ctgactaaaa g                           31

<210> SEQ ID NO 3
<211> LENGTH: 26
<212> TYPE: DNA
<213> ORGANISM: Artificial
<220> FEATURE:
<223> OTHER INFORMATION: Oligonucleotide

<400> SEQUENCE: 3
aaaaaatgac caagggctaa ttcact                                 26

<210> SEQ ID NO 4
<211> LENGTH: 26
<212> TYPE: DNA
<213> ORGANISM: Artificial
```